United States Patent
Chadli

(10) Patent No.: US 11,446,352 B2
(45) Date of Patent: Sep. 20, 2022

(54) COMPOSITIONS AND METHODS FOR INHIBITING TUMOR-INDUCED IMMUNE SUPPRESSION

(71) Applicant: Augusta University Research Institute, Inc., Augusta, GA (US)

(72) Inventor: Ahmed Chadli, Evan, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 0 days.

(21) Appl. No.: 16/180,203

(22) Filed: Nov. 5, 2018

(65) Prior Publication Data
US 2019/0134149 A1    May 9, 2019

Related U.S. Application Data

(60) Provisional application No. 62/581,269, filed on Nov. 3, 2017, provisional application No. 62/737,403, filed on Sep. 27, 2018.

(51) Int. Cl.
*A61K 38/12* (2006.01)
*A61P 35/00* (2006.01)
*A61K 31/664* (2006.01)

(52) U.S. Cl.
CPC .............. *A61K 38/12* (2013.01); *A61P 35/00* (2018.01); *A61K 31/664* (2013.01)

(58) Field of Classification Search
None
See application file for complete search history.

(56) References Cited

PUBLICATIONS

The National Cancer Institute (<https://training.seer.cancer.gov/disease/categories/tumors.html> Apr. 26, 2020).*
The Merck Manual (<https://www.merckmanuals.com/professional/pulmonary-disorders/environmental-pulmonary-diseases/mesothelioma> Apr. 26, 2020).*
Dornetshuber et al. ("Enniatin Exerts p53-Dependent Cytostatic and p53-Independent Cytotoxic Activities against Human Cancer Cells" Chem. Res. Toxicol. 2007, 20, 465-473).*
RxList (<https://www.rxlist.com/cytoxan-drug.htm>; Jun. 13, 2013).*
Merck Manual (<https://www.merckmanuals.com/professional/neurologic-disorders/intracranial-and-spinal-tumors/overview-of-intracranial-tumors> accessed Sep. 23, 2020).*
Watjen et al. ("Enniatins A1, B and B1 from endophytic strain of Fusarium tricinctum induce apoptotic cell death in H4IIE hepatoma cells accompanied by inhibition of ERK phosphorylation"; Mol. Nutr. Food Res. 2009, 53, 431-440).*
Walter et al. ("Single-dose cyclophosphamide synergized with immune responses to the renal cell cancer vaccine IMA901"; OncoImmunology 2:1, e22246, Jan. 2013).*
Barrot et al. (Hsp90, an unlikely ally in the war on cancer; FEBS Journal; 280(2013) 1381-1395).*
Solarova et al. (Hsp90 inhibitor as a sensitizer of cancer cells to different therapies (Review) International Journal of Oncology 46: 907-926:2015).*
Curran, M., et al., "PD-1 and CTLA-4 combination blockade expands infiltrating T cells and reduces regulatory T and myeloid cells within B16 melanoma tumors," PNAS, 107:4275-4280 (2010).
Krummel, M.F. and Allison, J.P., "CD18 and CTLA-4 have opposing effects on the response of T cells to stimulation," J. Exp. Med., 182:459-465 (1995).
Larkin, J., et al., "Combined Nivolumab and Ipilimumab or Monotherapy in Untreated Melanoma," N Engl J Med, 373:23-34 (2015).
Postow, M.A., et al., "Nivolumab and Ipilimumab versus Ipilimumab in Untreated Melanoma," N Engl J Med, 372:2006-2017 (2015).
Walanus, T.L., et al., "CTLA-4 can function as a negative regulator of T cell activation," Immunity, 1:405-413 (1994).
Wei, S.C., et al., "Distinct cellular mechanisms underlie anti-CTLA-4 and anti-PD-1 checkpoint blockade," Cell, 170:1120-1133 (2017).
Wolchok, J.D., et al., "Safety and clinical activity of combined PD-1 (nivolumab) and CTLA-4 (ipilimumab) blockade in advanced melanoma patients," N Engl J Med, 369:122-133 (2013).

* cited by examiner

*Primary Examiner* — Julie Ha
*Assistant Examiner* — Tara L Martinez
(74) *Attorney, Agent, or Firm* — Smith, Gambrell & Russell; Judy Jarecki-Black

(57) ABSTRACT

It has been discovered that the cyclic peptide EnnA inactivates the Hsp90 chaperone pathway, but without activating an extensive heat shock response and overexpression of anti-apoptotic proteins. Mechanistically distinct, EnnA inhibits Hsp90 and destabilize PDL-1 and IDO, two major immune checkpoints mediating tumor-induced immune suppression. The provided herein show that EnnA profoundly modulates the cytokine signature of cancer cells and promotes a cytokine profile that favors an immune attack on tumor cells. This translates into highly efficacious anti-tumor activity in vivo, which, when combined with a single dose of chemotherapy, completely reduced the tumor burden in experimental animals and instilled highly efficient immune memory against the primary tumor.

10 Claims, 31 Drawing Sheets

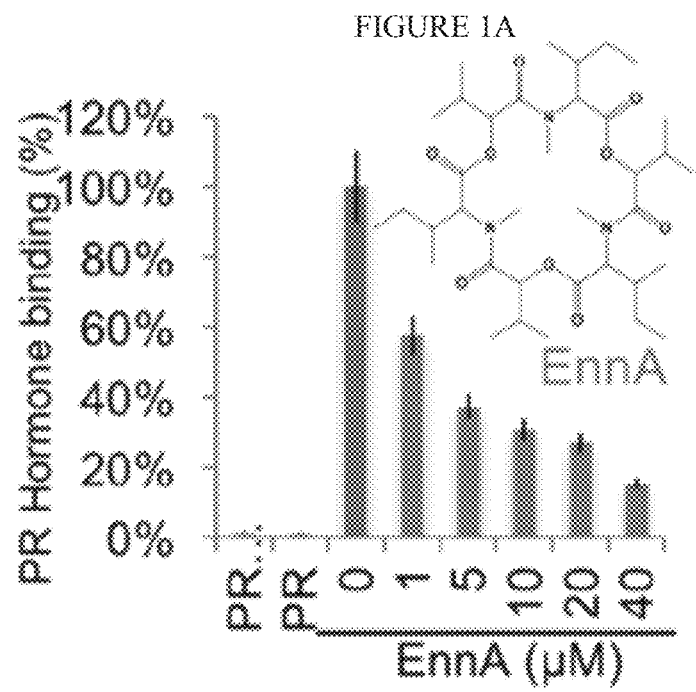
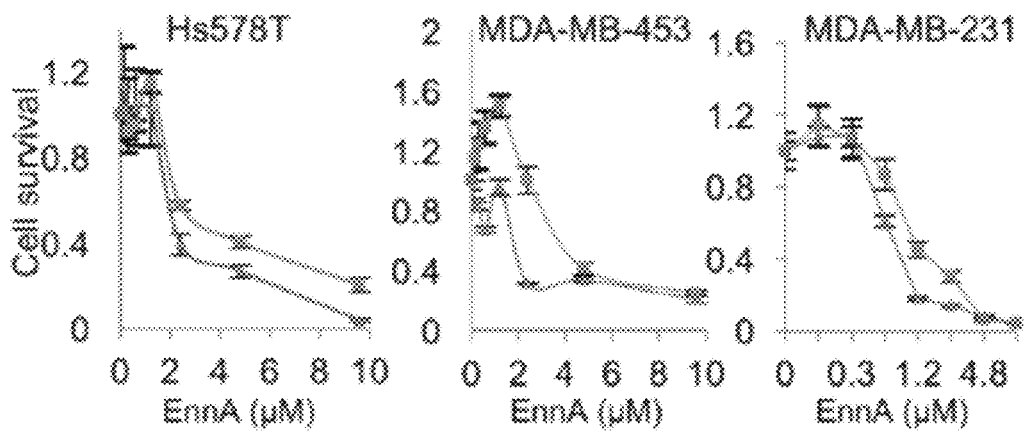

DMSO | EnnA

DMSO | EnnA

DMSO | EnnA (1.2μM)

Control- Cox4 | Control- LC3BII | Control- Merge + DAPI

DMSO

EnnA

DMSO

EnnA

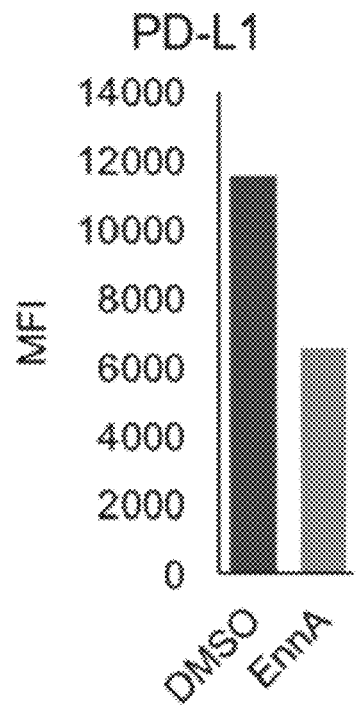
FIGURE 3C
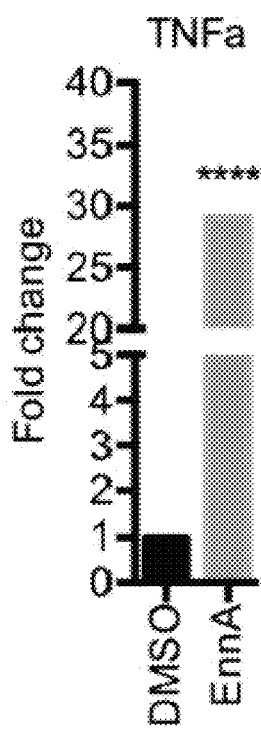 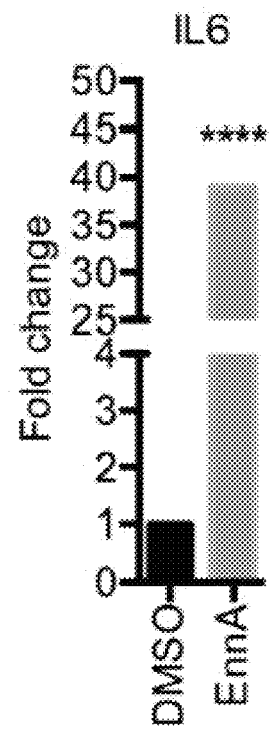  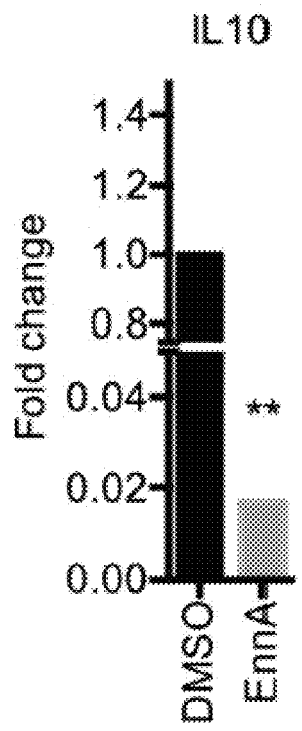
FIGURE 3D    FIGURE 3E    FIGURE 3F    FIGURE 3G

DMSO

EnnA

DMSO

EnnA

DMSO

EnnA

DMSO

EnnA

DMSO

EnnA

DMSO

EnnA

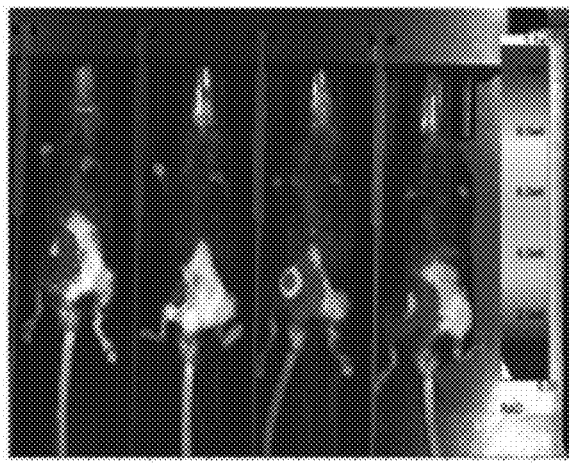
FIGURE 7A — Naïve T cells- Day 1
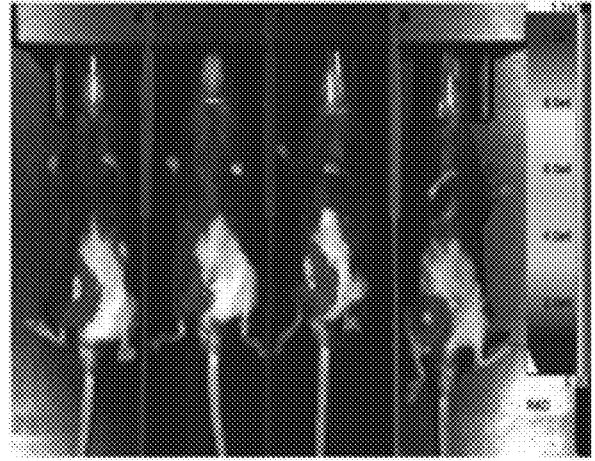
FIGURE 7B — Immune T cells- Day 1
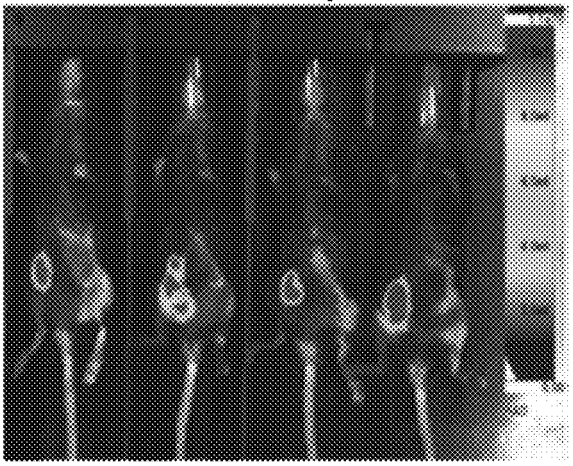
FIGURE 7C — Naïve T cells- Day 7
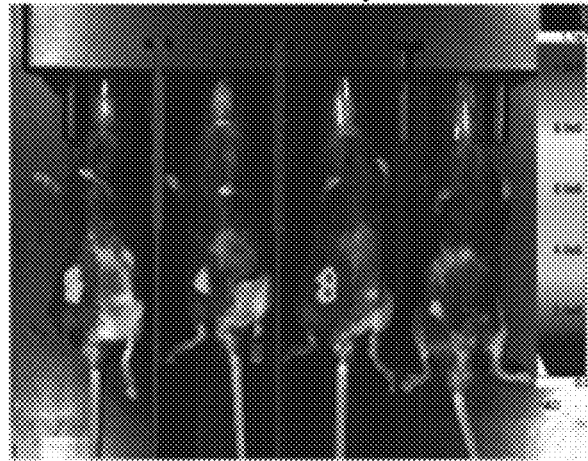
FIGURE 7D — Immune T cells- Day 7

DMSO- Merge (4x)

DMSO- Merge (40x)

EnnA- CD45 (4x)

EnnA- CD45 (40x)

EnnA- CD8b (4x)

EnnA- CD8b (40x)

DMSO

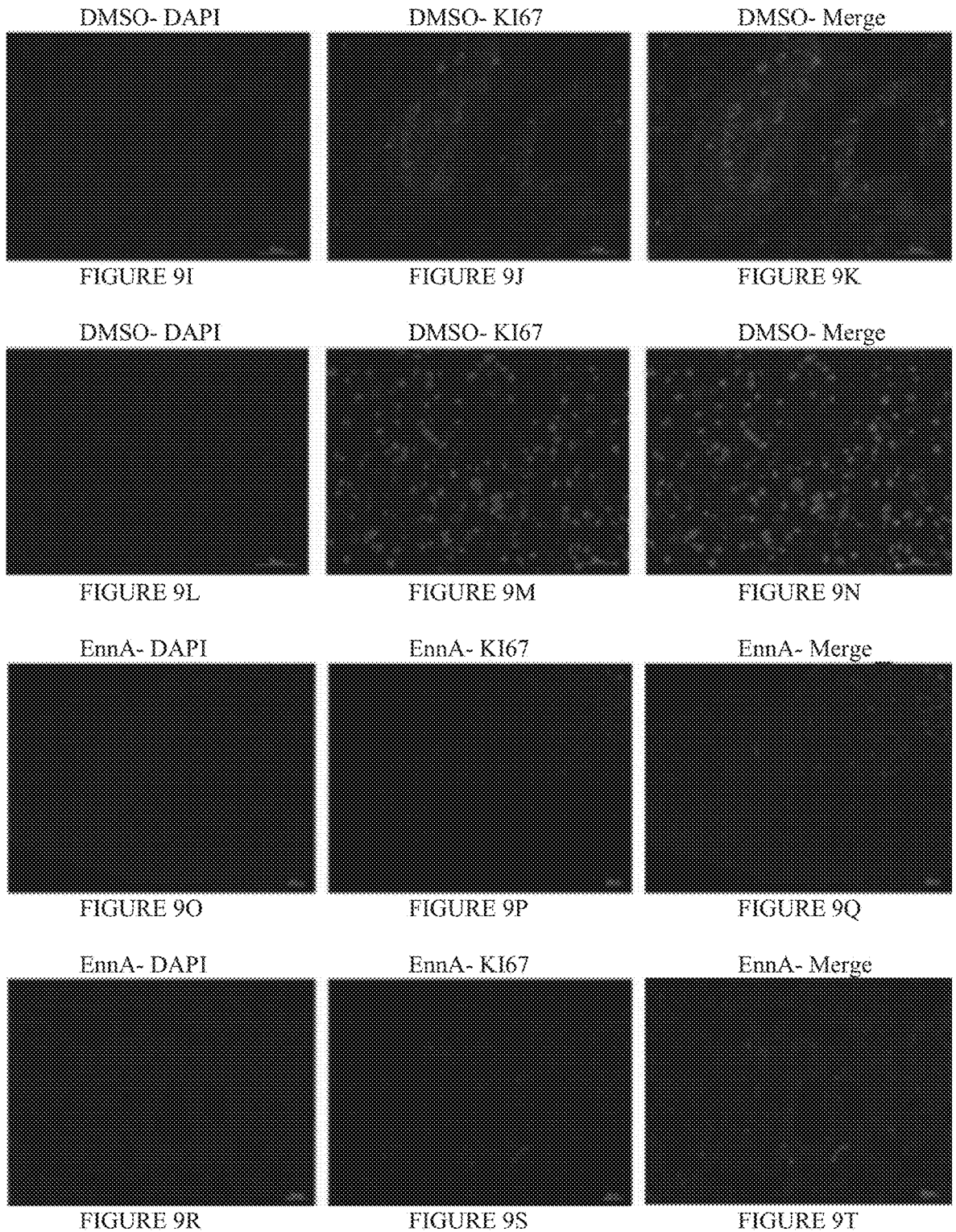

COMPOSITIONS AND METHODS FOR INHIBITING TUMOR-INDUCED IMMUNE SUPPRESSION

CROSS-REFERENCE TO RELATED APPLICATIONS

This application claims benefit of and priority to U.S. Provisional Patent Application No. 62/581,269 filed on Nov. 3, 2017, and 62/737,403 filed on Sep. 27, 2018, both of which are incorporated herein by reference in their entirety.

STATEMENT REGARDING FEDERALLY SPONSORED RESEARCH

This invention was made with government support under GM102443-01 awarded by the National Institutes of Health. The government has certain rights in the invention.

TECHNICAL FIELD OF THE INVENTION

The invention is directed to immunotherapies and methods of their use.

BACKGROUND OF THE INVENTION

Heat shock protein 90 (Hsp90) is a validated anti-cancer drug target. As a result, several inhibitors of Hsp90 ATPase activity are in clinical trials. These inhibitors cause proteasomal degradation of Hsp90 "client" proteins, thereby simultaneously inflicting a combinatorial inactivation of multiple oncogenic pathways. However, none of the first generation Hsp90 inhibitors has been Food and Drug Administration-approved for cancer therapy; in part because they counterproductively activate an extensive heat shock response and overexpression of the anti-apoptotic proteins Hsp70, Hsp40, and Hsp27.

Therefore it is an object of the invention to provide compositions and methods for inhibiting Hsp90 without activating a heat shock response and overexpression of anti-apoptotic proteins.

It is another object of the invention to provide methods and compositions for promoting or enhancing an immune response is a subject in need thereof.

It is still another object of the invention to provide methods and compositions for inhibiting tumor-induce immune suppression in a subject in need thereof.

It is yet another object to provide methods and compositions for inhibiting or reducing negative checkpoint regulators in the immune system of a subject.

It is still another object of the invention to provide compositions and methods for promoting long-term immune memory against tumors.

SUMMARY OF THE INVENTION

It has been discovered that the cyclic peptide Enniatin A (EnnA) inactivates the Hsp90 chaperone pathway, but without activating an extensive heat shock response and overexpression of anti-apoptotic proteins. Mechanistically distinct, EnnA inhibits Hsp90 machine and destabilizes PDL-1 and IDO, two major immune checkpoints mediating tumor-induced immune suppression. The data provided herein show that EnnA profoundly modulates the cytokine signature of cancer cells and promotes a cytokine profile that favors an immune attack on tumor cells. This translates into highly efficacious anti-tumor activity in immunocompetent mice, which, when combined with a single dose of chemotherapy, completely reduced the tumor burden in experimental animals and instilled highly efficient immune memory against the primary tumor.

One embodiment provides a pharmaceutical composition containing EnnA and a potentiating agent, a chemotherapeutic agent, or both. A preferred potentiating agent is cyclophosphamide. The pharmaceutical compositions can be formulated for enteral or parenteral administration.

One embodiment provides a method for reducing tumor burden in a subject in need thereof, by administering to the subject an effective amount of a composition containing EnnA optionally in combination or alternation with a potentiating agent, a chemotherapeutic agent, or both.

Another embodiment provides a method for inhibiting infiltration of regulatory T cells and MDSCS into tumor microenvironments by administering to a subject in need thereof and effective amount of Enniantin A, optionally in combination or alternation with a potentiating agent, a chemotherapeutic agent, or both.

Another embodiment provides a method for increasing immune memory to tumor antigens, by administering to a subject in need thereof an effective amount of Enniantin A, optionally in combination or alternation with a potentiating agent, a chemotherapeutic agent, or both.

Another embodiment provides a method for adoptive T cell therapy to reduce the tumor burden The disclosed methods and compositions can have one or more of the following effects when administered to a subject: inhibits or reduces proliferation of T regulatory cells in tumor microenvironments; reduces the mRNA and protein levels of Programmed death-ligand 1; inhibits the Hsp90 machine but does not induce an extensive cellular heat shock response; reduces proliferation of regulatory T cells in tumor microenvironments; reduces the number of CD4+Foxp3+ T regulatory cells (Tregs) in tumors; increases the immunogenicity of tumor cells; inhibition of IDO enzymatic activity, and induces or promotes immune memory; reduces the MDSCs (CD11b$^+$GR-1$^+$) in the tumor microenvironment; increase the level of GR-1$^-$CD11$^+$CD103$^+$ antigen presenting cells; induces immunogenic cells death.

BRIEF DESCRIPTION OF THE DRAWINGS

FIGS. 1C-1E are line graphs of cell survival versus EnnA concentration (µM) in breast cancer cell lines Hs578T (FIG. 1C), MDA-MB-2453 (FIG. 1D) and MDA-MB231 (FIG. 1E) upon treatment with EnnA for 48 and 72 h. FIGS. 1Q-1BB are fluorescence micrographs showing mitophagy in Hsp578T cells treated with EnnA as indicated by colocalization of the mitochondria marker Cox4 and the autophagy marker LC3BII.

FIG. 3C is a graph showing FACS analysis of PD-L1 level in AT3 cells. FIGS. 3D-3K are graphs showing qPCR analysis of the mRNA level of cytokines TNFa (FIG. 3D), IL-6 (FIG. 3E), TGFb1 (FIG. 3F) and IL-10 (FIG. 3G), the chemokines S100a9 (FIG. 3J) and CCL3 (FIG. 3K), as well as PDL1 (FIG. 3H) and IDO (FIG. 3I).

FIGS. 7A-7D are images of mice bearing E0071 tumors that received T cell adoptive transfer from tumor free mice (naïve T cells) or from tumor resistant mice (immune T cells) from FIGS. 6F-6I.

FIGS. 9C-9N show immunofluorescent staining of Ki67 in E0771 tumors from tumor bearing mice treated with DMSO. FIGS. 9O-9Z show immunofluorescent staining of Ki67 in E0771 tumors from tumor bearing mice treated with EnnA.

DETAILED DESCRIPTION OF THE INVENTION

I. Definitions

Figure 1F:
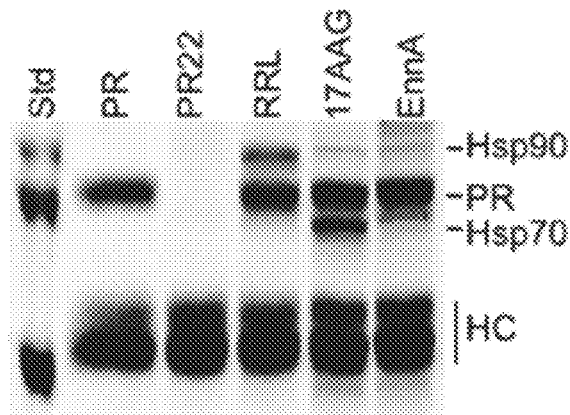
FIG. 1F shows SDS-PAGE and Coomassie blue staining of protein complexes analysis after PR reconstitution. PR alone (PR), antibody (PR22)+RRL, PR+RRL without inhibitor (RRL), PR+RRL with 1 µM 17-AAG (17AAG) PR+RRL with 10 µM BEAU or EnnA.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the term "cancer" refers to a neoplasm or tumor resulting from abnormal uncontrolled growth of cells. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

The term "tumor" refers to an abnormal mass of tissue that results when cells divide more than they should or do not die when they should. Tumors may be benign (not cancer), or malignant (cancer).

As used herein, an "immune cell" refers to any cell from the hemopoietic origin including, but not limited to, T cells, B cells, monocytes, dendritic cells, and macrophages.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and I-cells from an immunized syngeneic animal and measuring protective or therapeutic effect in a second subject.

As used herein, the terms "individual," "host," "subject,": and "patient" are used interchangeably herein, and refer to a mammal, including, but not limited to, humans, rodents, such as mice and rats, and other laboratory animals.

The term "potentiating agent" refers to a drug or agent that when combined with another drug or agent results in a pharmacologic response greater than the sum of individual responses to each drug or agent.

II. EnnA Compositions

Compositions containing EnnA are provided. In one embodiment, the compositions are pharmaceutical compositions used for the treatment of cancer or for the reduction of tumor burden in a subject. The compositions optionally include a potentiating agent, for example cyclophosphamide, or a chemotherapeutic agent. It has been discovered that EnnA kills cancer cells in vivo and in vitro through inhibition of the Hsp90 chaperoning machine, without inducing the counterproductive heat shock response that hampered the first generation of Hsp90 inhibitors. EnnA also modulates the cancer cell cytokine profile to become more immunogenic and promotes a tumor microenvironment that favors T cell-mediated attack by reducing the levels of Programed Death ligand 1 (PDL-1 or PD-L1) and IDO in malignant cells. Significantly, combination of EnnA with a one-time dose of chemotherapy cures mice and protects them from a secondary assault with primary tumor cells.

A. EnnA

Figures 1G, 1H, 1I:
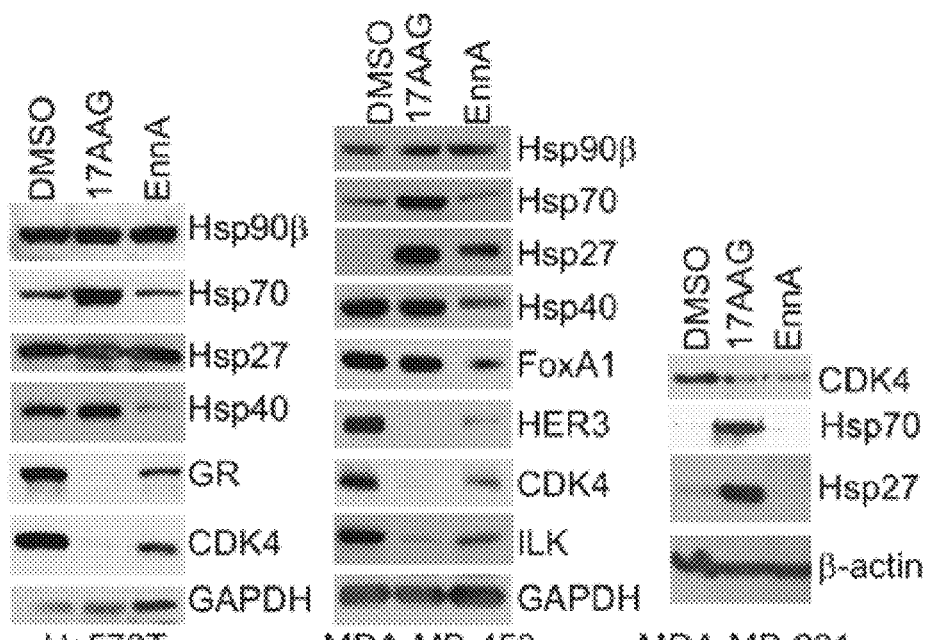
FIGS. 1G-1I are autoradiographs of Western blots of cytosols from various cell lines treated with 17-AAG (1 µM) or EnnA (3 µM) with antibodies against the specified proteins.
Figure 1J:
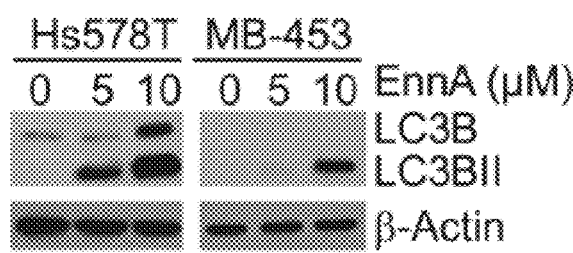
FIG. 1J is an autoradiograph showing EnnA causes autophagy in Hs578T and MDA-MB453 cell lines.
Figure 1K:
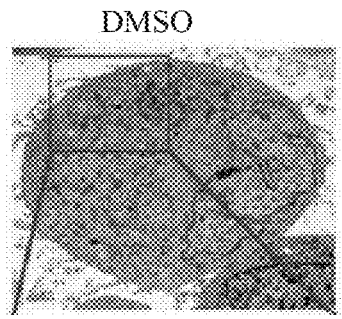
FIGS. 1K-1N are electron microscopy micrographs showing autophagosomes and reduced mitochondria content in Hs578T cells treated with DMSO or EnnA.
Figure 1L:
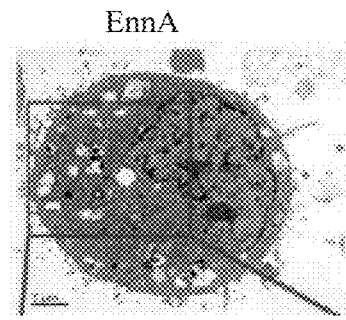
Figure 1M:
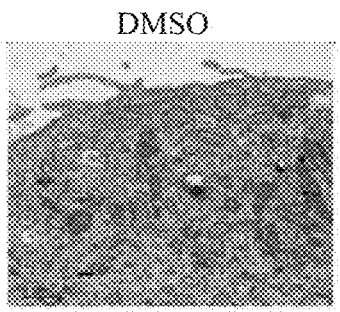
Figure 1N:
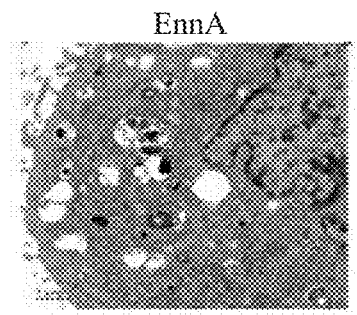
Figure 1O:
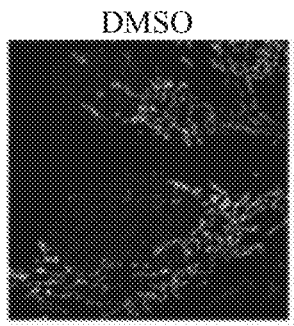
FIGS. 1O-1P are fluorescence micrographs showing EnnA causing reduced mitochondria content in Hs578T cells.
Figure 1P:
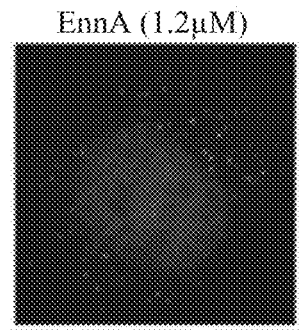
Figure 1Q:
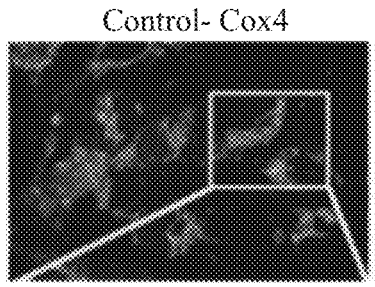
Figure 1R:
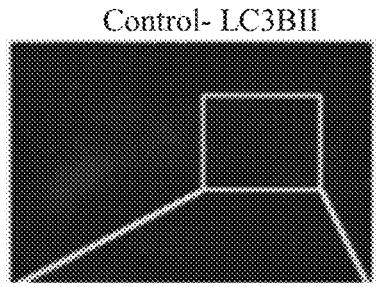
Figure 1S:
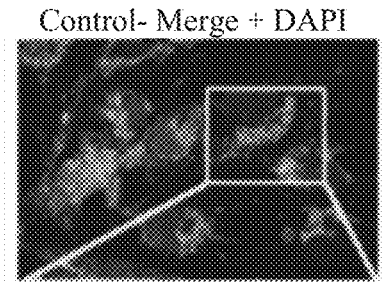
Figures 1T, 1U, 1V:
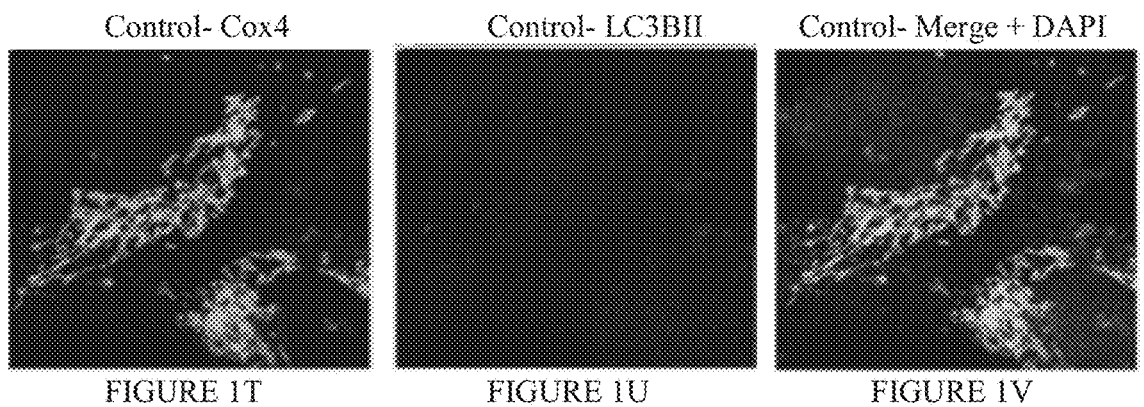
Figures 1W, 1X, 1Y:
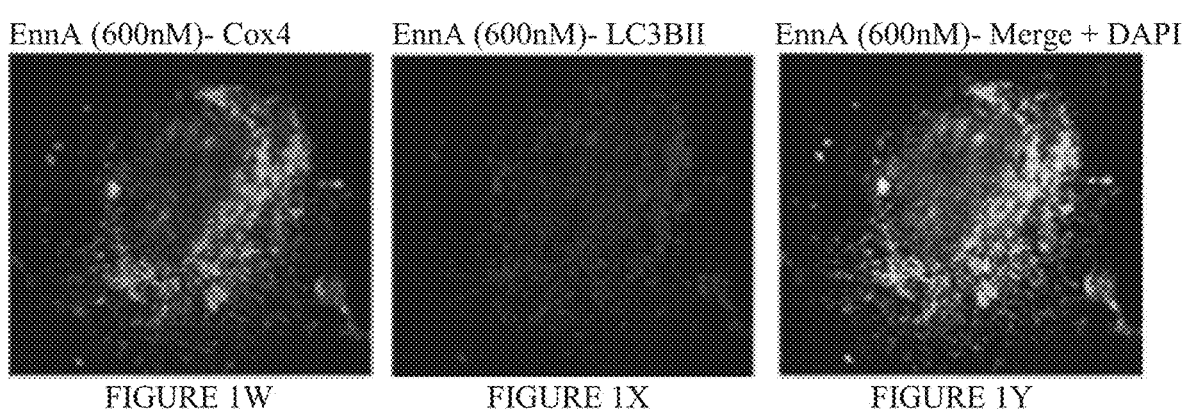
Figures 1A, 1B, 1Z:
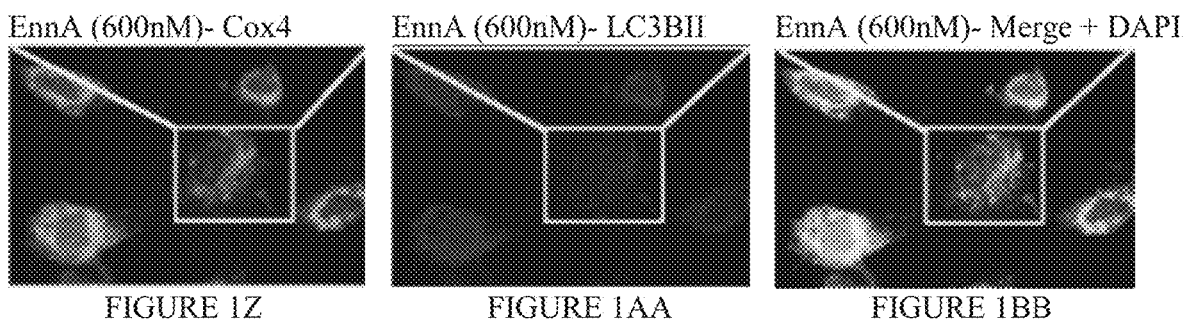
FIG. 1A shows the structure of EnnA.
FIG. 1B is a graph of PR hormone binding (%) versus EnnA concentration (µM) and shows a dose-dependent effect of EnnA on progesterone receptor (PR) chaperoning using reticulocyte lysate (RRL). The first bar indicates 100% folding activity of RRL without inhibitor. PR22 indicates the antibody without PR but with RRL and EnnA. PR represents the antibody (PR22) with PR but without RRL. All other samples have PR22, PR, and RRL without (first bar) or with increased concentration of EnnA.
Figure 2A:
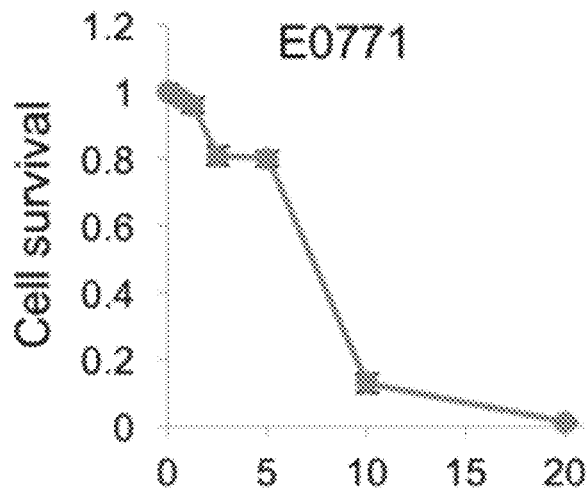
FIGS. 2A-2D are line graphs of cell survival versus EnnA concentration and shows survival of murine breast cancer cell line E0771 (FIG. 2A), EMT6 (FIG. 2B), AT3 (FIG. 2C), and 4T1 (FIG. 2D) upon treatment with EnnA for 72 h.
Figure 2B:
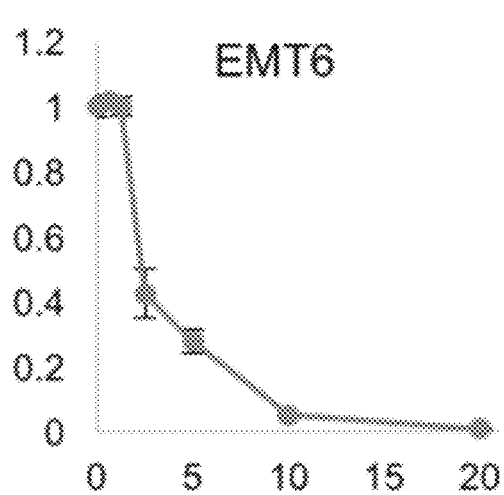
Figure 2C:
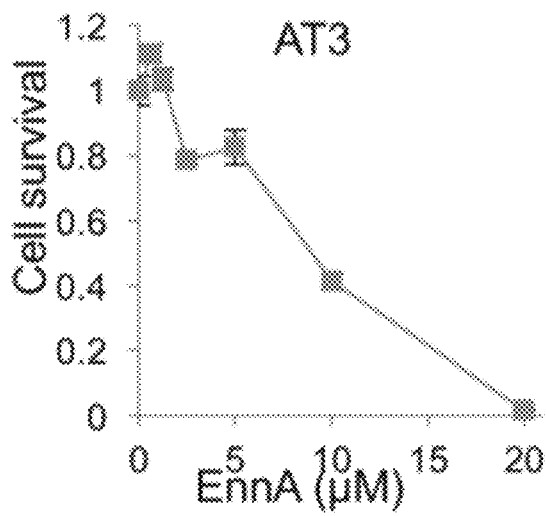
Figure 2D:
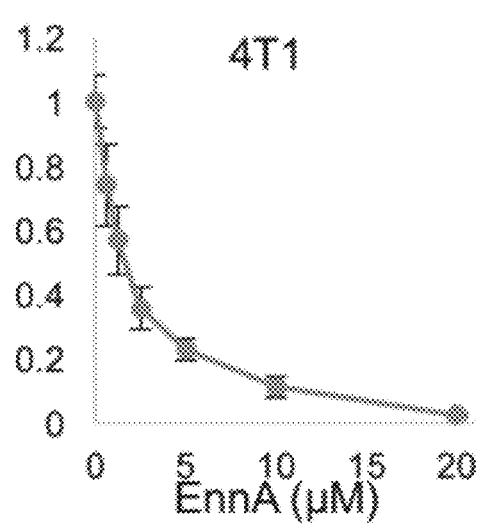
Figure 2E:
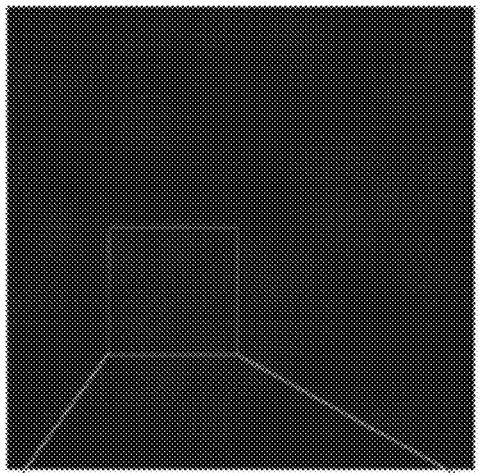
FIG. 2E-2H are fluorescence micrographs showing EnnA induces autophagy in E0771 cells.
Figure 2F:
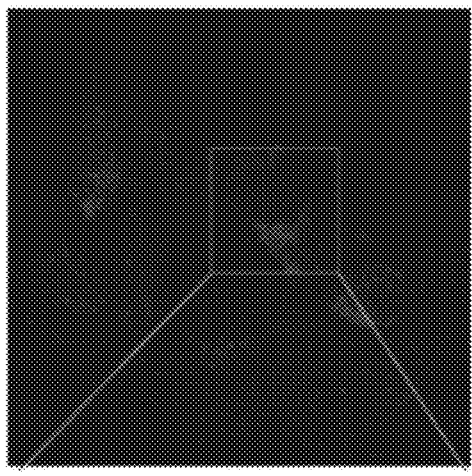
Figure 2G:
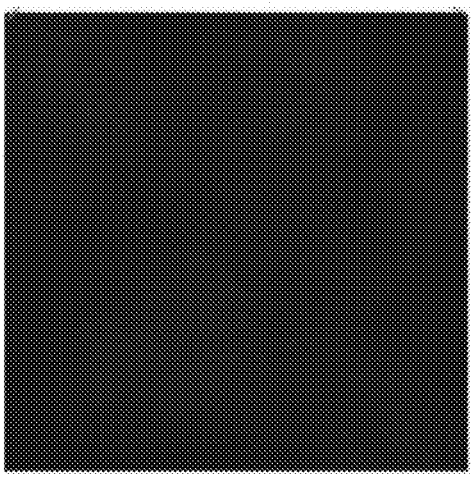
Figure 2H:
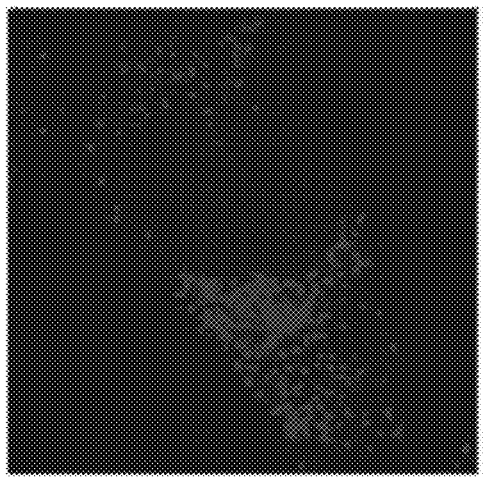
Figures 2I, 2J:
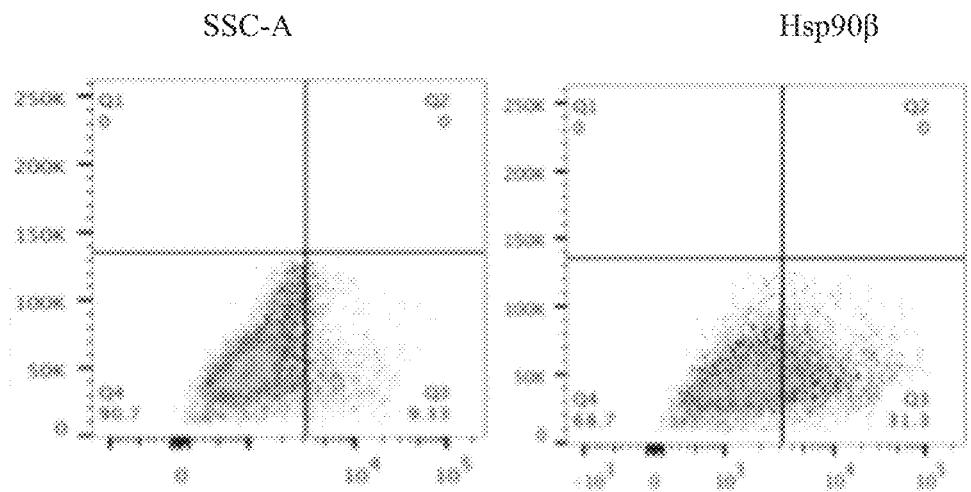
FIGS. 2I-2K show FACS analysis of Hsp90β expression on the cell surface of E0771 cells treated with DMSO or EnnA.
Figure 2K:
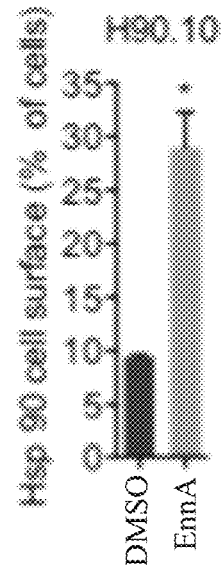
Figure 2L:
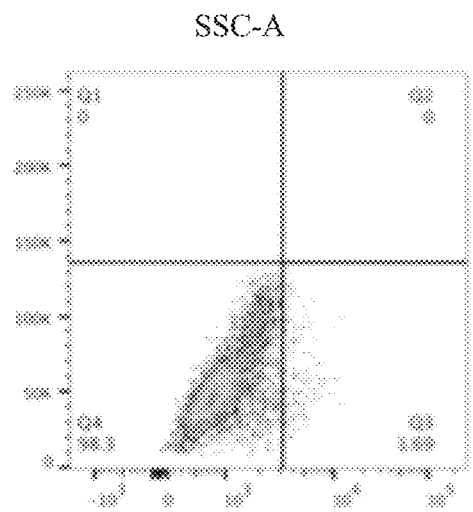
FIGS. 2L-2N show FACS analysis of the ratio of Hsp90α to Hsp90β expression on the cell surface of E0771 cells treated with DMSO or EnnA.
Figure 2M:
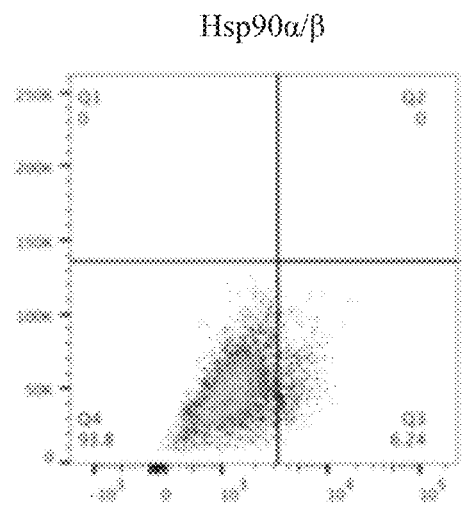
Figure 2N:
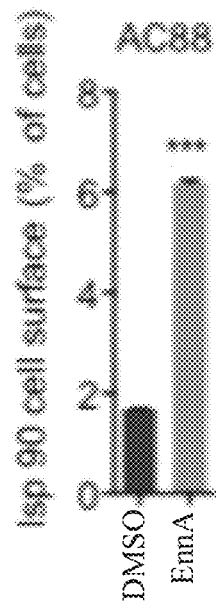
Figure 2O:
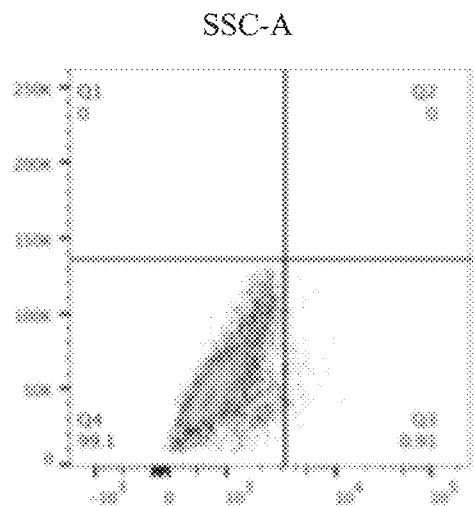
FIGS. 2O-2Q show FACS analysis of Hsp90α expression on the cell surface of E0771 cells treated with DMSO or EnnA.
Figure 2P:
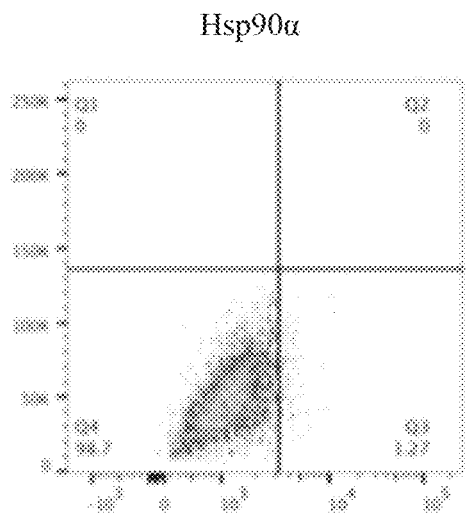
Figure 2Q:
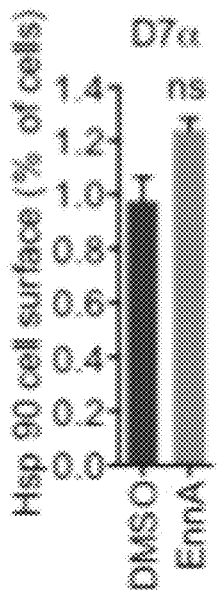
Figure 2R:
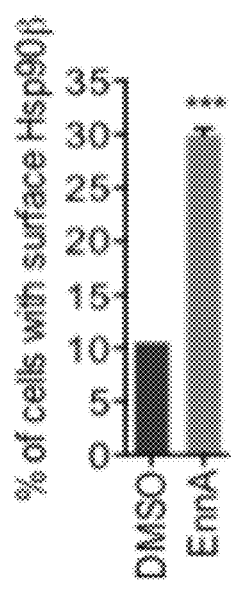
FIG. 2R is a bar graph showing expression of Hsp90β on the surface of AT3 cells treated with DMSO or EnnA.
Figure 2S:
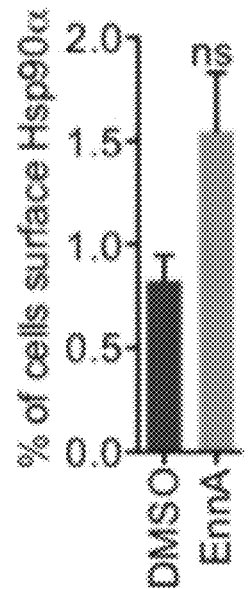
FIG. 2S is a bar graph showing expression of Hsp90α on the surface of AT3 cells treated with DMSO or EnnA.
Figure 2T:
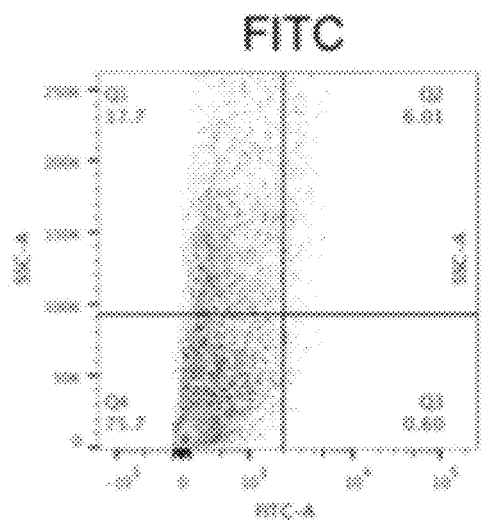
FIGS. 2T-2X show FACS analysis of Hsp90β expression on the surface of E0771 tumor cells treated with mIgG, DMSO, or EnnA.
Figure 2U:
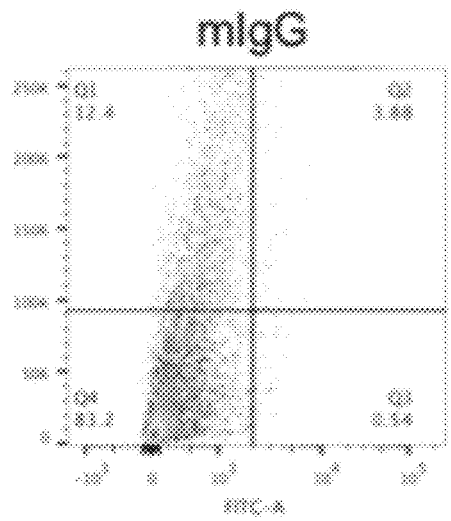
Figure 2V:
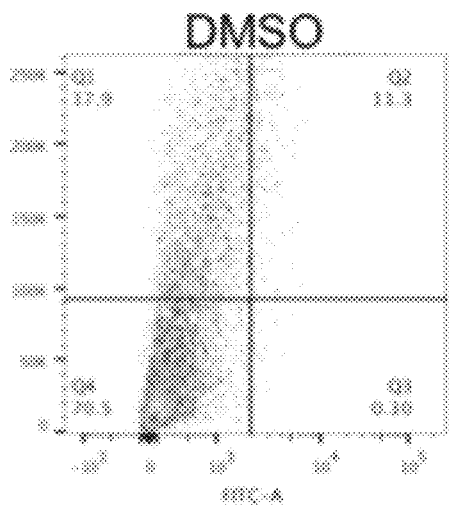
Figure 2W:
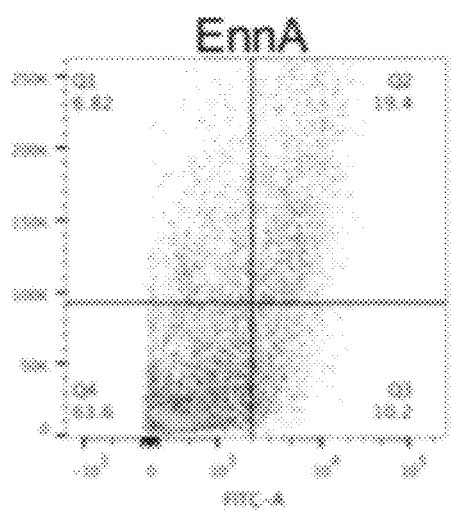
Figure 2X:
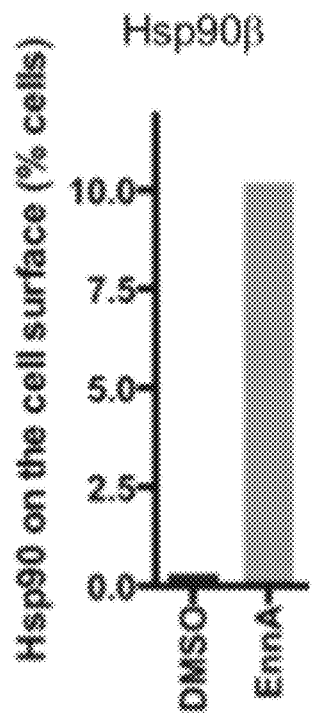

The structure of EnnA is shown in FIG. 1A, EnnA has antifungal and antibiotic activity, and the EnnA-based drug fusafungine is clinically used for upper respiratory tract infections. Although the molecular target of EnnA remains unknown, it has shown ionophoric properties, and affects several signaling pathways that are essential for cancer cell survival. In preclinical studies, the analogue Enniatin B demonstruated anti-angiogenic activity and synergizes with sorafenib, a kinase inhibitor used in the clinic to treat various malignancies, to reduce tumor growth of the KB-3-1 cervix carcinoma.

B. Pharmaceutical Compositions

One embodiment provides pharmaceutical compositions containing EnnA and optionally a chemotherapeutic agent, a potentiating agent, or both. The pharmaceutical compositions can be formulated for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. The precise dosage will vary according to a variety of factors such as subject-dependent variables (e.g., age, immune system health, etc.), the disease, and the treatment being effected.

For the disclosed compositions, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 20 mg/kg of body weight daily of the compositions are administered to mammals, preferably to a human subject. Generally, for intravenous injection or infusion, dosage may be lower.

In certain embodiments, the compositions are administered locally, for example by injection directly into a site to be treated. Typically, the injection causes an increased localized concentration of the immunomodulatory agent composition which is greater than that which can be achieved by systemic administration. The compositions can be combined with a matrix to assist in creating an increased localized concentration of the compositions by reducing the passive diffusion of the compositions out of the site to be treated.

1. Formulations for Parenteral Administration

In some embodiments, compositions disclosed herein are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In some embodiments the compositions are formulated for oral delivery. Oral solid dosage forms are described generally in Remington's Pharmaceutical Sciences, 18th Ed. 1990 (Mack Publishing Co, Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed, (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The compositions can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

The disclosed compositions can be applied topically. Topical administration may not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Treatment

1. Therapeutic Strategies

Methods of inducing or enhancing an immune response in a subject are provided. Typically, the methods include administering to a subject an effective amount of EnnA, optionally in combination or alternation with a potentiating agent and/or a therapeutic agent including a chemotherapeutic agent. In one embodiment, the effective amount of EnnA is formulated as a pharmaceutical composition. The immune response can be, for example, inhibition of suppressive immune signals from for example, Treg and myeloid-derived suppressor cells (MDSC) at a tumor sites.

In some embodiments, the EnnA compositions can inhibit, reduce, or block infiltration of suppressive immune cells in tumor microenvironments. In another embodiment, the EnnA compositions can be used to inhibit, reduce, or block tumor metastasis. In some embodiments, the agent can reduce or inhibit the activity of Tregs, reduce the production of cytokines such as IL-10 from Tregs, reduce the differentiation of Tregs, reduce the number of Tregs, reduce the ratio of Tregs within an immune cell population, or reduce the survival of Tregs.

The methods can be used in vivo or ex vivo to inhibit, reduce, or block suppressive immune responses and thereby have an immune-stimulating therapeutic effect.

In some embodiments, the EnnA composition is administered directly to the subject. In some embodiments, the EnnA compositions is contacted with cells (e.g., immune cells) ex vivo, and the treat cells are administered to the subject (e.g., adoptive transfer). The EnnA compositions can enable a more robust immune response to be possible. The disclosed compositions are useful to stimulate or enhance immune responses involving T cells by inhibiting, reducing or blocking suppressive immune signal transduction.

2. Subjects to be Treated a. Treatment of Cancer

The disclosed EnnA compositions and methods can be used to treat cancer. Generally, the agents are used to stimulate or enhance an immune response to cancer in the subject by administering to the subject an amount of an EnnA composition. The method can reduce or more symptoms of the cancer.

In one embodiment the EnnA compositions inhibit, reduce, or block Treg and MDSC suppressive functions at a tumor site.

Cancer cells acquire a characteristic set of functional capabilities during their development through various mechanisms. Such capabilities include evading apoptosis, self-sufficiency in growth signals, insensitivity to anti-growth signals, tissue invasion/metastasis, limitless replicative potential, and sustained angiogenesis. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

The disclosed compositions and methods are particularly useful for the treatment of cancers that are associated with cells that express abnormally high levels of PD-L1.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (AIX) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma; osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

b. Tumor Burden

One embodiment provides a method for reducing tumor burden in a subject in need thereof by administering the disclosed EnnA compositions optionally including a potentiating agent, a chemotherapeutic agent or both.

One embodiment provides a method for killing tumor cells in a subject in need thereof by administering to the subject and effective amount of the disclosed EnnA compositions to kill the tumor cells.

The disclosed methods and compositions can have one or more of the following effects when administered to a subject: inhibits or reduces proliferation of T regulatory cells in tumor microenvironments; reduces the mRNA and protein levels of Programmed death-ligand 1; inhibits the Hsp90 machine but does not induce an extensive cellular heat shock response; reduces proliferation of regulatory T cells in tumor microenvironments; reduces the number of CD4+Foxp3+ T regulatory cells (Tregs) in tumors; reduce the number of CD11b+Gr-1+ MDSCs, increase the number of GR-1-CD11+CD103+ antigen presenting cells, increases the immunogenicity of tumor cells; inhibits IDO enzymatic activity, induces or promotes immune memory, and adoptive T cells transfer from resistant subject in protective for naïve animals.

IV. Co-Therapies

The disclosed EnnA compositions can be administered to a subject in need thereof alone or in combination with one or more additional therapeutic agents. In some embodiments, the EnnA composition and the additional therapeutic agent are administered separately, but simultaneously or in alternation. The EnnA composition and the additional therapeutic agent can also be administered as part of the same composition. In other embodiments, the EnnA composition and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The EnnA composition can be the first or the second therapeutic agent.

The EnnA composition and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response, for example by inhibiting a suppressive immune response.

A. Antimicrobials

The EnnA compositions can be administered to the subject in combination with an antimicrobial such as an antibiotic, an antifungal, an antiviral, an antiparasitics, or essential oil.

In some embodiments, the subject is administered the EnnA compositions and/or the antimicrobial at time of admission to the hospital to prevent further bacterial, fungal or viral complications. The antibiotic can target pathogens and the EnnA compositions can stimulate the immune system, for example by inhibiting a suppressive immune response or inducing immunogenic cell death.

B. Chemotherapeutic Agents

The EnnA compositions can be combined with one or more chemotherapeutic agents and/or pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

C. Other Immunomodulators

1. PD-1 Antagonists

In some embodiments, the EnnA compositions are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U.S.A*, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor.

Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332, 582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, and 9,492,540, all of which are incorporated by reference in their entireties.

See also Berger et al., Clin. Cancer Res., 14:30443051 (2008).

Exemplary anti-B7-H1 (also referred to as anti-PD-L1) antibodies include, but are not limited to, those described in the following U.S. Pat. Nos. 8,383,796, 9,102,725, 9,273, 135, 9,393,301, and 9,580,507 all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147 all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists, Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest, 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

2. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., Clinical Kidney Journal, 3(2):135-137 (2010), published online December 2009.

In other embodiments, the antagonist is a small molecule. A series of small organic compounds have been shown to bind to the B7-1 ligand to prevent binding to CTLA4 (see Erbe et al., J. Biol. Chem., 277:7363-7368 (2002). Such small organics could be administered alone or together with an anti-CTLA4 antibody to reduce inhibitory signal transduction of T cells.

3. IDO Inhibitors

In some embodiments, the optional therapeutic agents include one or more IDO inhibitors. The IDO protein, or indoleamine (2,3)-dioxygenase, has been identified as a checkpoint protein involved in generating the immunosuppressive tumor microenvironment that supports tumor growth. The enzyme has 2 isoforms, IDO1 and IDO2, that act as the first step in the metabolic pathway that breaks down the essential amino acid tryptophan. Representative IDO inhibitors include, but are not limited to D-1MT (indoximod), L-1MT, MTH-Trp, β-carbolines, Naphthoquinone-based, S-allyl-brassinin, S-benzyl-brassinin, 5-Bromo-brassinin, Phenylimidazole-based, 4-phenylimidazole, Exiguamine A, NSC401366, and NLG802.

4. Potentiating Agents

In some embodiments, the optional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(-)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

Although CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode &. Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg, (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al, *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is sub-therapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16), anthracyclines, oxaliplatin, doxorubicin, TLR4 antagonists, and IL-18 antagonists.

VI. Kits

The disclosed EnnA compositions can be packaged in a hermetically sealed container, such as an ampoule or sachette, indicating the quantity. The agent can be supplied as a dry sterilized lyophilized powder or water free concentrate in a hermetically sealed container and can be reconstituted, e.g., with water or saline to the appropriate concentration for administration to a subject. For example, the agent can be supplied as a dry sterile lyophilized powder in a hermetically sealed container at a unit dosage of at least 5 mg, or at least 10 mg, at least 15 mg, at least 25 mg, at least 35 mg, at least 45 mg, at least 50 mg, or at least 75 mg. The lyophilized agent can be stored at between 2 and 8° C. in their original container and are typically administered within 12 hours, or within 6 hours, or within 5 hours, or within 3 hours, or within 1 hour after being reconstituted.

In an alternative embodiment, the EnnA compositions are supplied in liquid form in a hermetically sealed container indicating the quantity and concentration. In some embodiments, the liquid form of the EnnA composition supplied in a hermetically sealed container including at least 1 mg/ml, or at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the agent.

Pharmaceutical packs and kits including one or more containers filled with agent are also provided. Additionally, one or more other prophylactic or therapeutic agents useful for the treatment of a disease can also be included in the pharmaceutical pack or kit. The pharmaceutical pack or kit can also include one or more containers filled with one or more of the ingredients of the disclosed pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits designed for the above-described methods are also provided. Embodiments typically include one or more EnnA compositions. In particular embodiments, a kit also includes one or more other prophylactic or therapeutic agents useful for the treatment of cancer, in one or more containers.

EXAMPLES

Example 1

Identification of Enniatin (EnnA) as Hsp90 Machine Inhibitor

Materials and Methods

A cell-free high-throughput screen (HTS) platform based on the progesterone receptor (PR) using reticulocyte lysate (RRL) as a source of molecular chaperones was used to screen 175 natural products (Patwardhan C A, et al., J Biomol Screen (2014)). This assay captures the physiological steps of PR refolding by the Hsp90 chaperoning machine and measures the recovery of its hormone-binding activities after mild heat treatment. It has the ability to identify inhibitors as well as activators of the core components of the Hsp90 chaperoning machine (i.e., Hsp90, Hsp70, Hsp40, Hsp90/Hsp70 organizing protein (HOP), and p23), including compounds that target chaperone complexes as well as individual proteins.

Results

The cyclohexadepsipeptide EnnA (FIG. 1A) was identified as an inhibitor of Hsp90 chaperoning machine in vitro. EnnA shows concentration-dependent inhibition of PR hormone binding recovery (FIG. 1B). Protein complex analysis shows that EnnA modifies the PR complexes in a manner distinct from that induced by the N-terminal Hsp90 inhibitor, 17-AAG (FIG. 3C-3E). Indeed, EnnA reduces the level of Hsp90 in PR complexes; however, it does not induce the accumulation of Hsp70-rich complexes observed with 17-AAG.

At the molecular level, all the signaling pathways inhibited by EnnA involve protein clients of Hsp90, such as ERK, PI3K/AKT, and p53. Interestingly, EnnA and antagonists of Hsp90 cause the mitochondrial membrane potential to collapse. These reports suggest that EnnA interferes with the Hsp90 machine function in cells.

EnnA exhibits potent and concentration-dependent cytotoxicity against the Hs578T triple-negative and MDA-MB-231 as well as the HER2+ MAD-MB-453 cell lines (FIG. 1G-1I). EnnA inactivation of the Hsp90 machine is demonstrated by destabilization of several relevant Hsp90 client proteins (FIG. 1F). The mechanism of action of EnnA appears to be different from that of 17-AAG. Indeed, EnnA does not induce overexpression of Hsp70 in all cell lines tested. Hsp27 is slightly induced in MAD-MB-453 cells, but a much lesser extent than 17-AAG. Furthermore, while 17-AAG induces apoptosis (not shown), EnnA induces autophagy in Hs587T and MDA-MB-453 cell lines (FIG. 1J). Further analysis showed that EnnA reduces mitochondria content in cancer cells (FIG. 1K-1P) through induction of mitophagy (FIG. 1Q-1BB). These findings indicate that EnnA inhibits the Hsp90 machine but does not induce an extensive cellular heat shock response, suggesting that EnnA may have pharmacological advantages over the classical N-terminal inhibitors of Hsp90. Further studies studies using murine breast cancer cells lines have shown that EnnA kills E0771, AT3, EMT6 and 4T1 in vitro (FIG. 2A-2D). As shown for human cell lines, EnnA induces autophagy in E0771 (FIG. 1J). MTT cell proliferation assay showed that, in vitro, EnnA kills E0771 and AT3 cells with an IC50 of about 5-10 µM, and EMT6 and 4T1 with an IC50 of about 2.5 µM. As in FIG. 1F, G, EnnA induces autophagy in E0771 murine cells (FIG. 2E-2H).

FACS analysis showing that EnnA induces exposure of Hsp90β to the surface of cancer treated cells in vitro (cell culture of E0771 (FIGS. 2I-2Q) and AT3 (2R-2S)) and in vivo (E0771 tumors (FIGS. 2T-2X)). It important to mention that Hsp90 exposure to the surface of cells is linked to immunogenic cell death. This suggest a role for Hsp90 bound to EnnA in antigen cross-presentation, which is an important mechanism for CD8+ T cell activation by antigen presenting cells (APCs) (see model, in FIG. 8W).

Example 2

EnnA Kills Murine Breast Cancer Cells In Vitro and Renders Them Potentially More Immunogenic Materials and Methods To validate EnnA's anti-tumor activity in vivo, a syngeneic mouse model using murine breast cancer E0771 and AT3 cell lines, which are tumorigenic in the C57/BL6 background, and the EMT6 cell line, which is tumorigenic in the Balb/C background was used.

Results

Figures 3A, 3B:
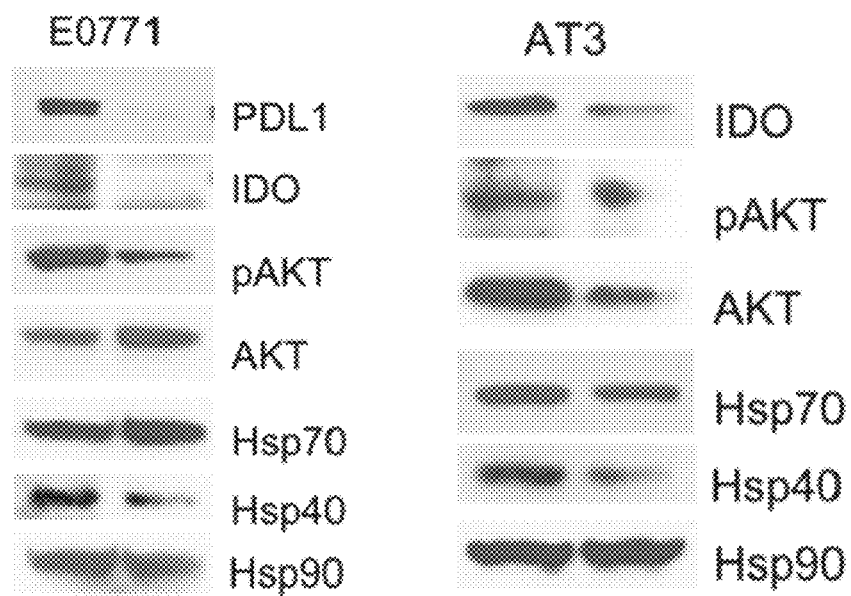
FIG. 3A-3B are autoradiographs of a Western blot showing expression of the indicated proteins in control (left lane) and 0.5 μM EnnA-treated (right lane) E0771 (FIG. 3A) and AT3 (FIG. 3B) cells.
Figure 3H:
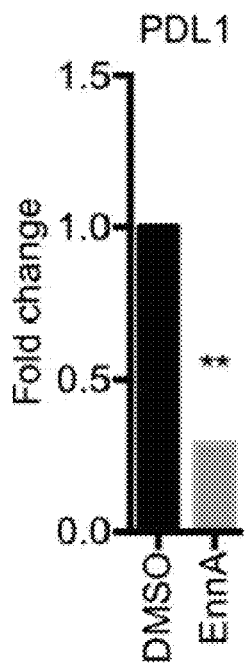
Figure 3I:
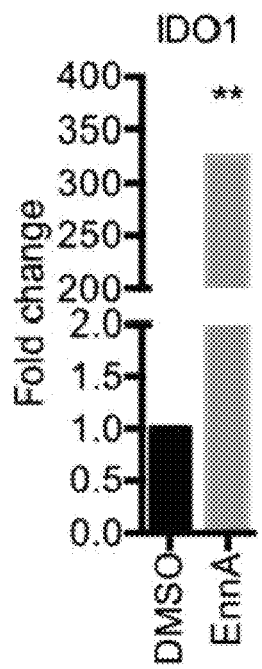
Figure 3J:
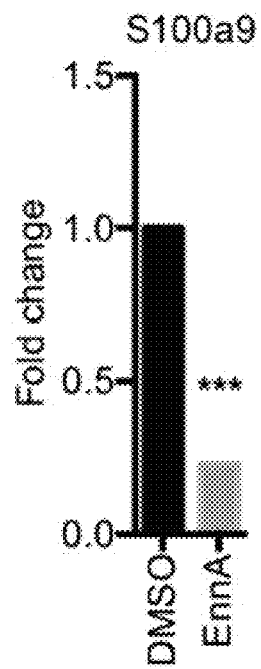
Figure 3K:
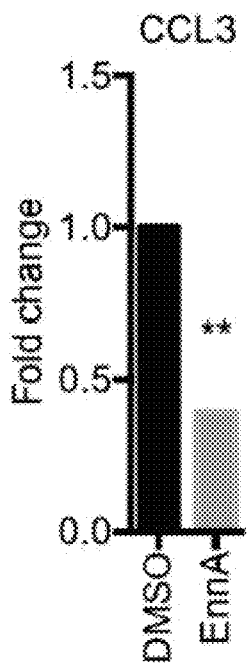
Figures 3L, 3M, 3N:
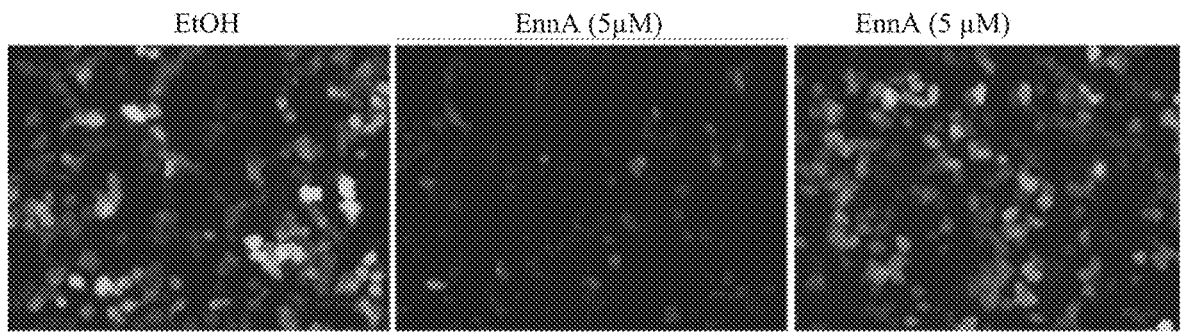
FIGS. 3L-3Q are micrographs of HEK293 cells transiently transfected with GFP-IDO fusion protein expressing or GFP alone plasmids for 24 h. Cells were then treated with 5 μM EnnA for 6 h and analyzed for green fluorescence and bright light.
Figures 3O, 3P, 3Q:
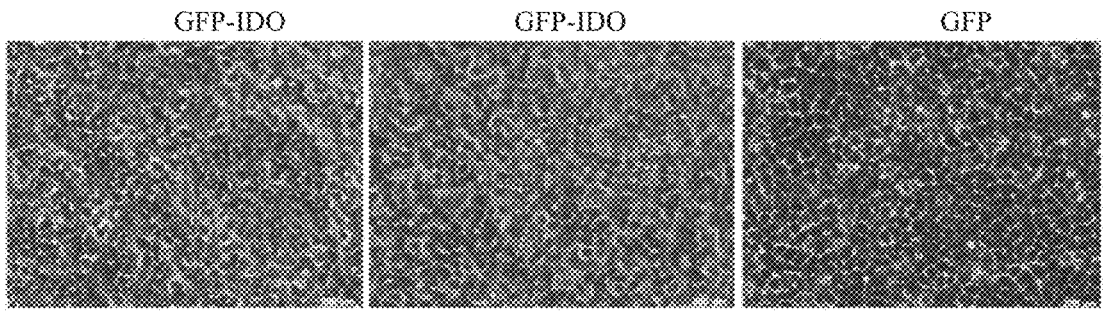
Figure 3R:
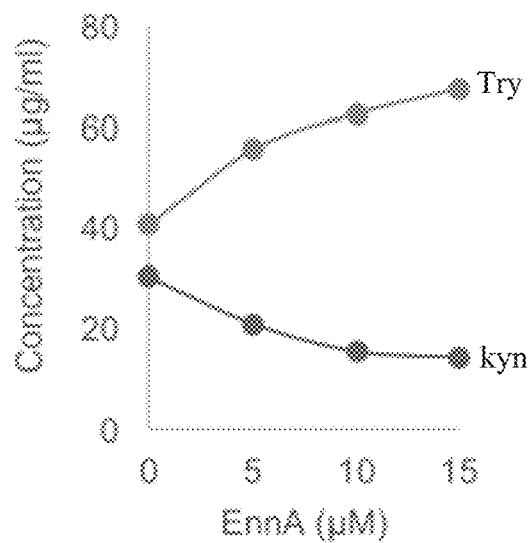
FIG. 3R is a line graph of μg/ml of tryptophan and its IDO-mediated product kynurenine using the previously reported HPLC-based assay.

Western blot analysis (FIG. 3A-3B) confirmed that EnnA destabilizes pAKT and reduces the protein expression of Hsp40 in E0771 and AT3. Hsp70 is reduced in AT3 but is slightly increased in E0771. Unexpectedly, EnnA causes a significant increase in mRNA expression of the pro-inflammatory cytokines TNFα, TGFβ, and IL-6 and reduces the level of anti-inflammatory IL-10 (FIG. 3D-3G). It also reduces the mRNA level of the chemokines S100a9 and CCL3 (FIG. 3J-3K). Importantly, EnnA reduces the mRNA and protein levels of the key immunological checkpoint component PDL-1 (FIG. 3H). Similar results were obtained with EMT6 (not shown). Furthermore, although EnnA highly increased the mRNA expression of another key immunological checkpoint, indolamine 2,3 dioxygenase (MO), (FIG. 3I), its protein level is severely reduced (FIG. 3A). This striking result was confirmed using an independent system where IDO is overexpressed as a GFP fusion protein (IDO-GFP) in HEK 293 cells. As shown in FIG. 3L-3N, short treatment (6 h) with EnnA caused a dramatic loss of IDO-GFP green fluorescence, while the CAT control showed no change. Furthermore, loss of IDO-GFP correlates with a loss of IDO enzymatic activity, as reflected by accumulation of tryptophan and reduction of its IDO-mediated product kynurenine in the culture media (FIG. 3R). No significant cell death was noticed at this early time point (6 h) (FIG. 3O-3Q).

This reduction in the protein levels of PDL-1 and IDO suggests that E0771 treated with EnnA would have a reduced ability to induce proliferation of regulatory T cells (Tregs) and would reduce their ability to maintain a suppressive tumor microenvironment.

Example 3

EnnA Displays a Robust Anti-Tumor Activity that Requires a Functional Immune System Materials and Methods 50,000 E0771 cells were surgically implanted in mammary fad pad of 10 C57BL/6 immunocompetent mice and 10 immunocompromised nude mice. 12 days after surgery, B6 and nude mice were divided into two groups each. the EnnA group was injected with 10 mg/kg of EnnA every other day, and the control group received a mixture of 15% DMSO and 20% cremophor in PBS.

Figure 4A:
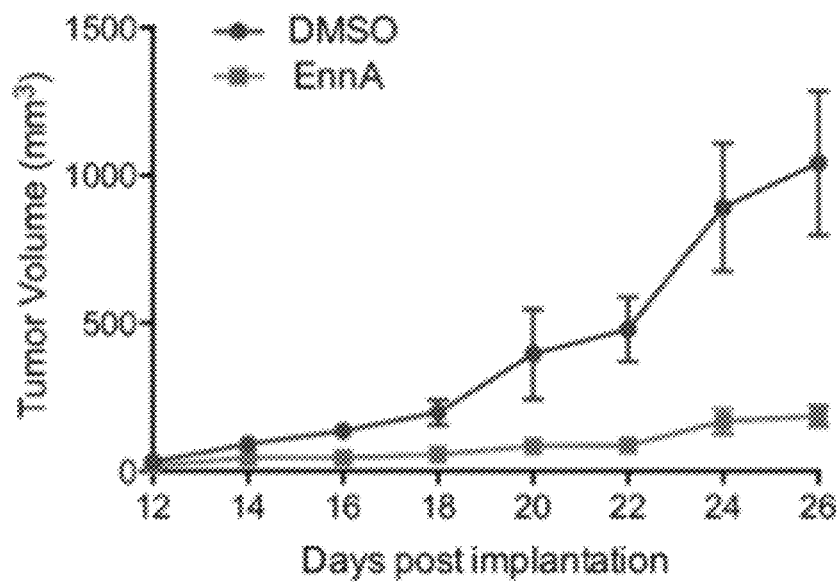
FIG. 4A. is a line graph of tumor volume (mm$^3$) versus day post implantation of E0771 in C57BL/6 immunocompetent mice.
Figure 4B:
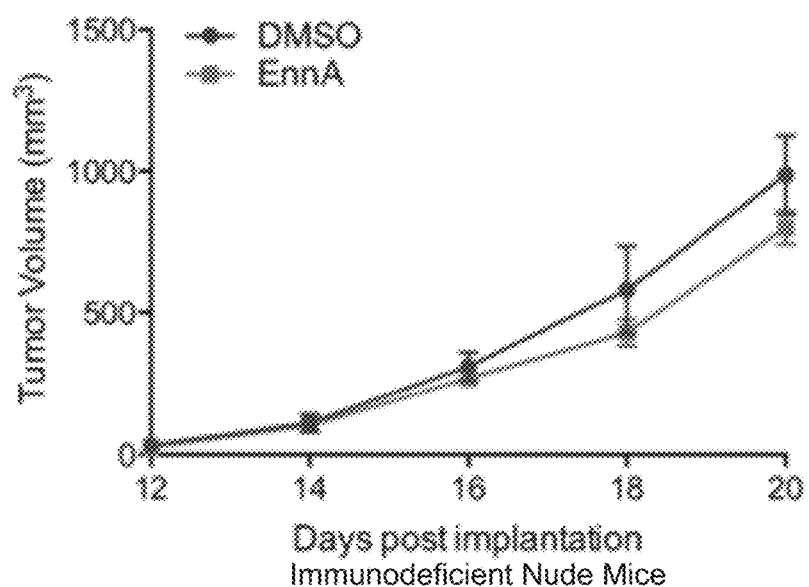
FIG. 4B is a line graph of tumor volume (mm$^3$) versus 5 day post implantation of E0771 in immunodeficient nude mice.
Figure 4C:
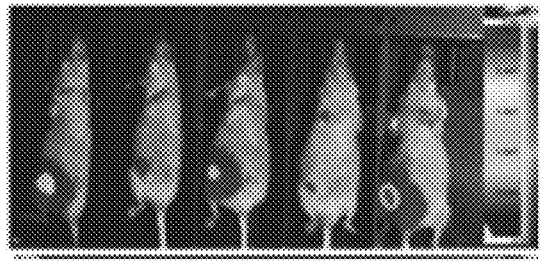
FIGS. 4C-4F are images of 5 representative nude mice from each indicated group seven and sixteen days post implantation of E0771 cells.
Figure 4D:
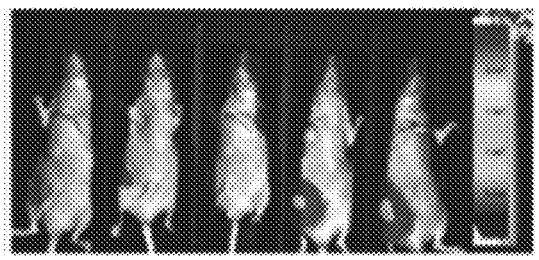
Figure 4E:
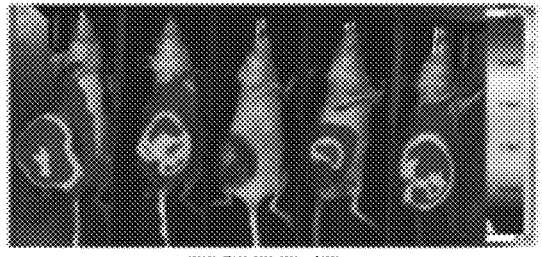
Figure 4F:
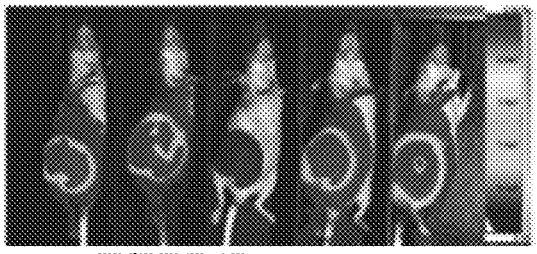

Results:

In vivo studies using E0771 and C57BL/6 immunocompetent mice showed that indeed, EnnA has powerful anti-tumor activity (FIG. 4A). Strikingly, no significant anti-tumor activity has been observed in the immunocompromised nude mice (FIGS. 4B-4F). These findings clearly demonstrated that the immune system plays a key role in the antitumor activity of EnnA.

Example 4

The Robust Anti-Tumor Activity of EnnA in Syngeneic Mouse Models Involves Inactivation of the Hsp90 Machine and Alteration of the Immune Tumor Microenvironment Materials and Methods 100,000 E0771 cells were surgically implanted in mammary fat pad of 20 mice. Ten days after surgery, mice were divided into two groups: the EnnA group was injected with 10 mg/kg of EnnA every other day, and the control group received a mixture of 15% DMSO and 20% cremophor in PBS.

Results

Figure 5A:
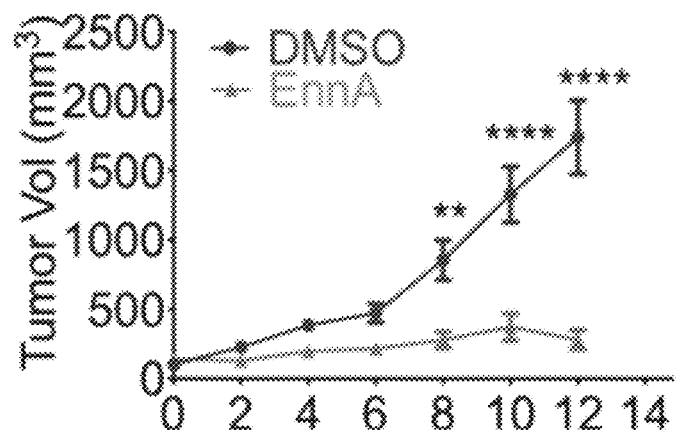
FIG. 5A is a line graph of tumor volume (mm$^3$) versus time (days) of mice injected with 100,000 E0771. Ten days after surgery, mice were divided into two groups: the EnnA group was injected with 10 mg/kg of EnnA. every other day, and the control group received a mixture of 15% DMSO and 20% cremophor in PBS.
Figure 5B:
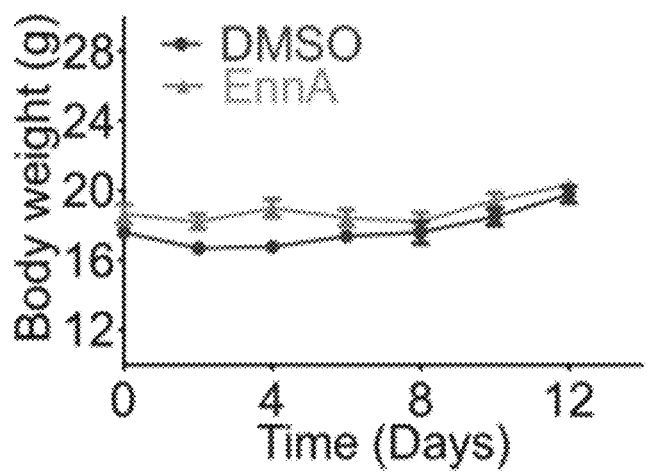
FIG. 5B is a line graph of body weight versus time (days) of mice treated with DMSO or EnnA.
Figure 5C:
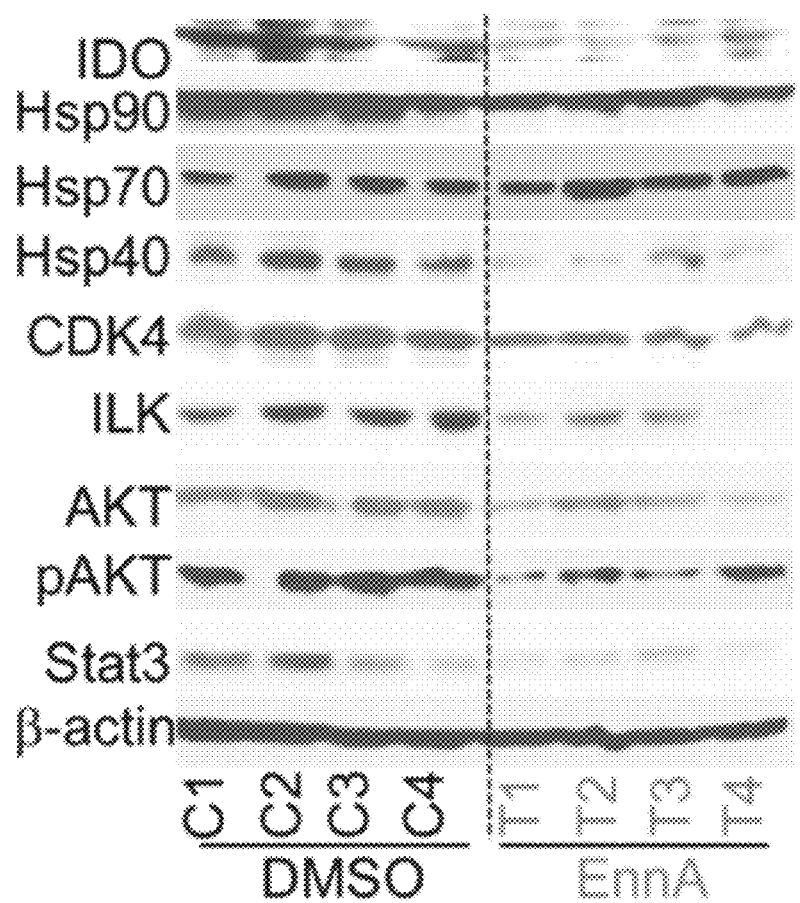
FIG. 5C is autoradiograph of a Western blot of four animals from each group using the indicated specific antibodies.
Figure 5D:
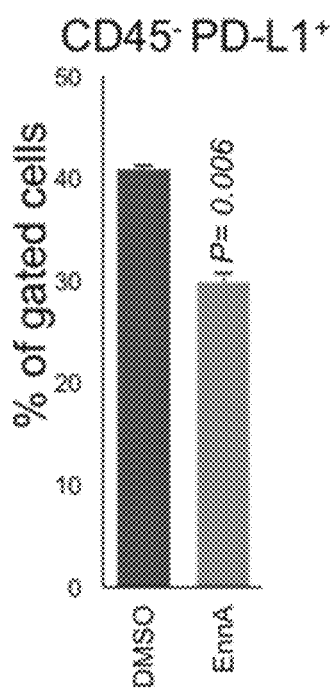
FIG. 5D is a bar graph of % of gated cells treated with DMSO or EnnA showing FACS analysis of tumor cells for PDL1.
Figure 5E:
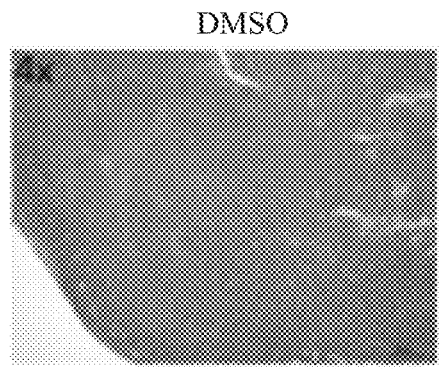
FIG. 5E-5J is a panel of micrographs showing immunohistochemistry analysis of H&E staining of tumors from control and EnnA mice for analysis of necrotic tissue.
Figure 5F:
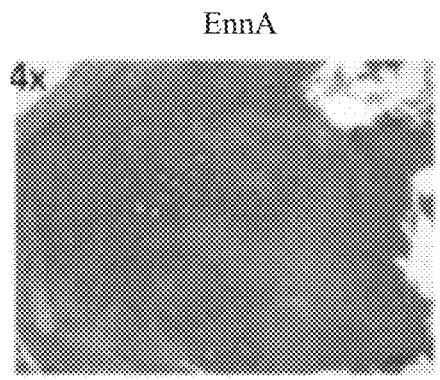
Figure 5G:
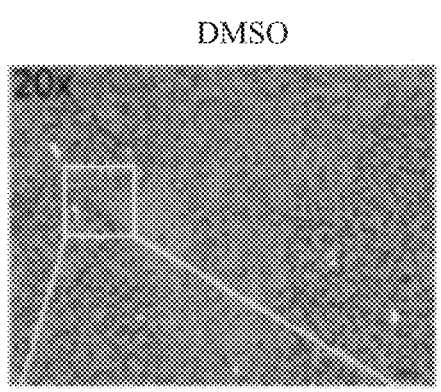
Figure 5H:
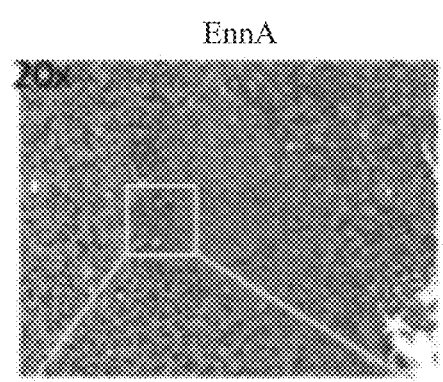
Figure 5I:
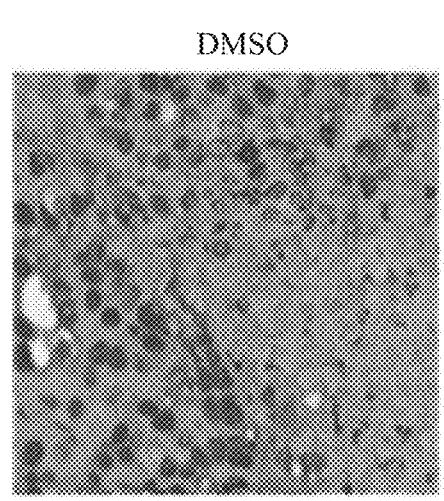
Figure 5J:
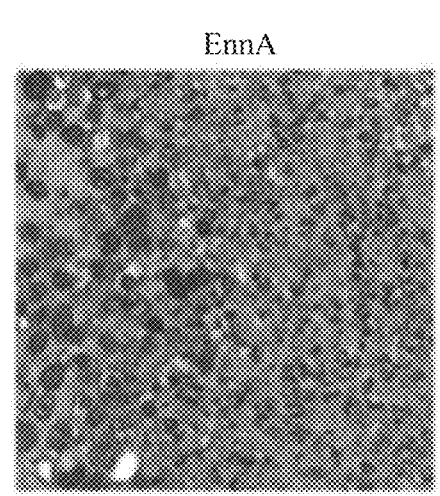
Figure 5K:
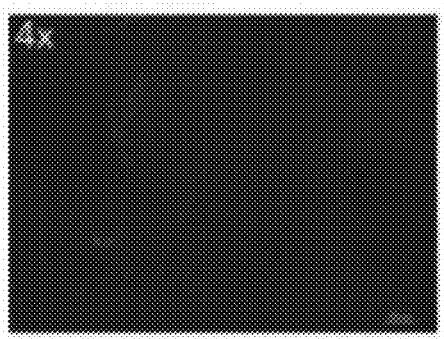
FIGS. 5K-5P is a panel of micrographs showing immunohistochemistry analysis of tumors from control and EnnA mice for analysis of immune cells infiltration using anti-CD45 antibody.
Figure 5L:
Figure 5M:
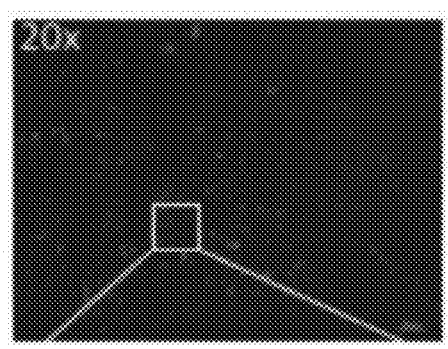
Figure 5N:
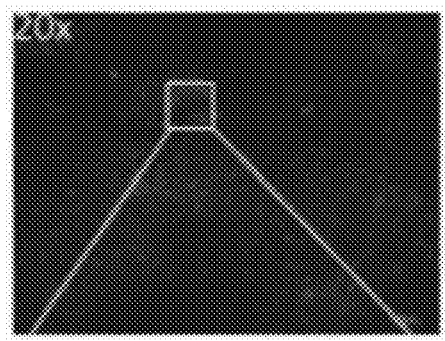
Figure 5O:
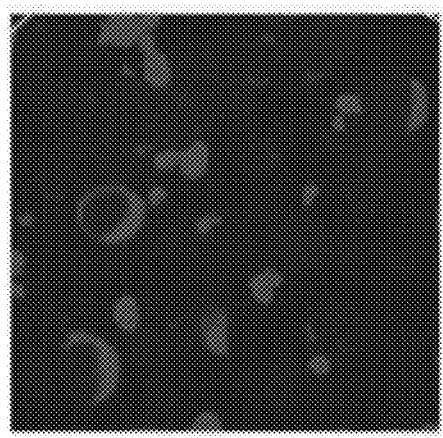
Figure 5P:
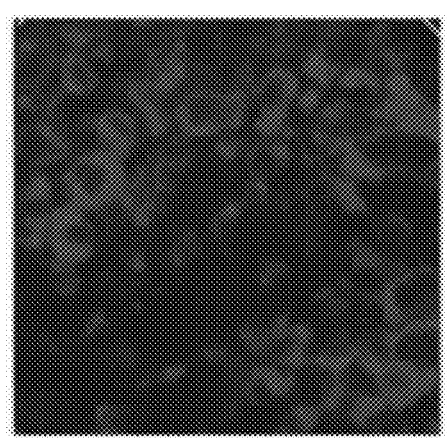
Figures 5Q, 5R, 5S, 5T:
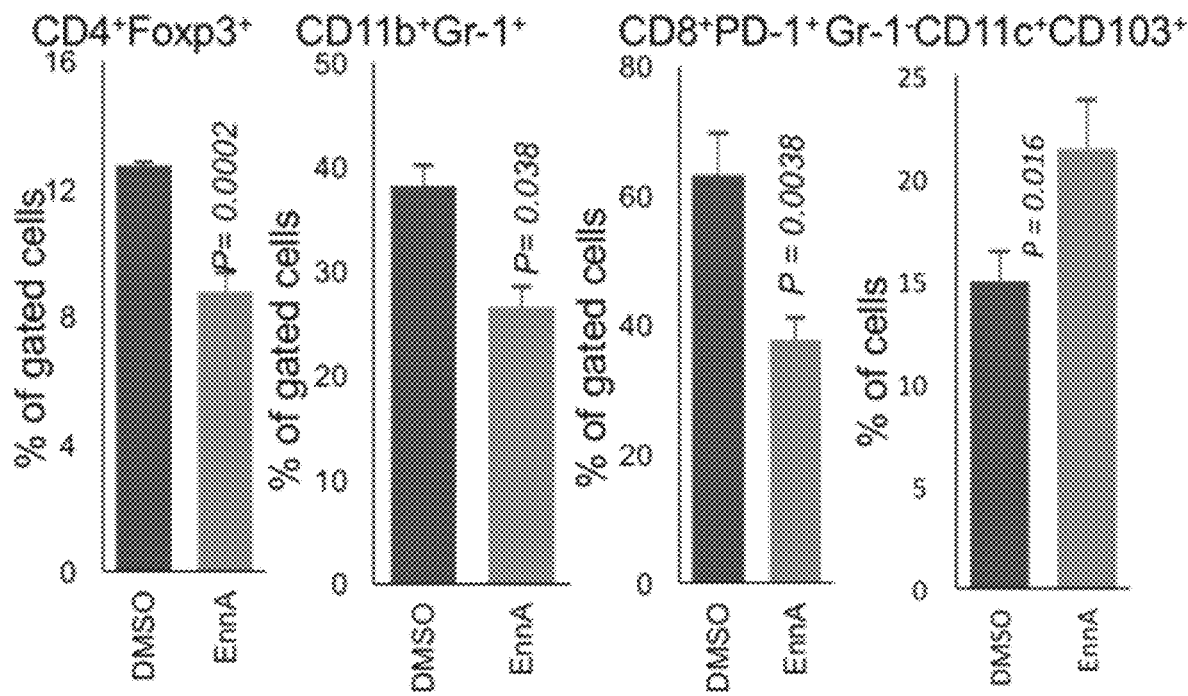
FIG. 5Q is a bar graph of % of gated cells treated with DMSO showing that EnnA treatment reduces CD4+/Foxp3+ Tregs.
FIG. 5R is a bar graph of % of gated cells treated with DMSO or EnnA showing that EnnA treatment reduces CD11b+Gr-1+ MDSCs.
FIG. 5S is a bar graph of % of gated cells treated with DMSO or EnnA showing that EnnA treatment reduces the number of CD8+/PD-1+ lymphocytes.
FIG. 5T is a bar graph of % of cells treated with DMSO or EnnA showing that EnnA treatment increase the number of GR-1-CD11c+CD103+ lymphocytes.

In vivo studies using E0771 and C57BL/6 immunocompetent mice showed that indeed, EnnA has powerful anti-tumor activity (FIG. 4A, 5A). No significant effect has been observed on the bodyweight (FIG. 5B) or activities of mice, indicating that the dose of EnnA used is not toxic. In correlation with the in vitro data, Western blot analysis showed that Hsp90 client proteins are destabilized in tumors from EnnA-treated mice (FIG. 5C), indicating that EnnA is targeting the Hsp90 machine in vivo. Furthermore, EnnA also destabilizes PD-L1 and IDO in vivo (FIG. 5C-5D). EnnA-exposed tumors are heavily necrotic, with a massive infiltration by T lymphocytes (FIG. 5E-5P). In addition, EnnA significantly reduced the number of CD4+Foxp3+ T regulatory cells (Tregs) in tumors (FIG. 5Q) and MDSCs (FIG. 5R). Infiltrating CD8+ lymphocytes have lower levels of PD-1 expression (FIG. 5S), suggesting that they are less exhausted and more active in killing cancer cells.

Example 5

EnnA is More Efficacious than 17AAG, and Synergizes with CPA to Kill Breast Cancer Tumors in Mice Materials and Methods Groups of mice (n=10) were implanted with 50,000 E0771 cells. When tumors were about 150 mm3 in volume (10 days post-implantation), mice were injected every other day with DMSO, EnnA (10 mg/Kg) or 17-AAG (10 mg/Kg). Two extra groups were made. In one group, EnnA was combined with one dose (150 mg/Kg) of cyclophosphamide (CPA) on day 14. In the other EnnA was combined with anti-CD8 antibody (250 µg/mouse) injected on day 18 and 22.

Results

Figure 6A:
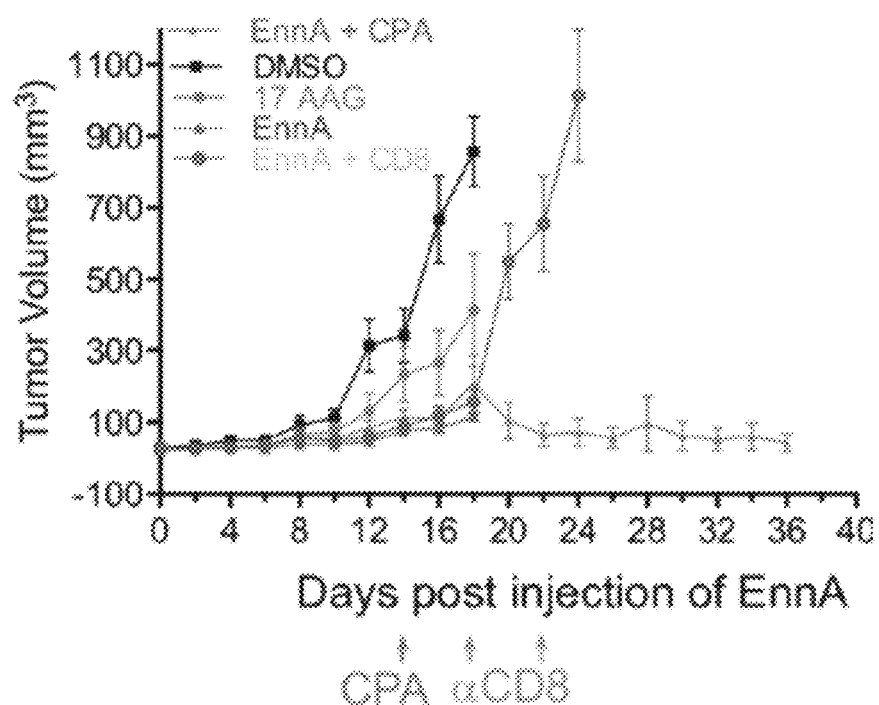
FIG. 6A is a line graph of tumor volume (mm$^3$) versus days post implantation.
Figures 6B, 6C:
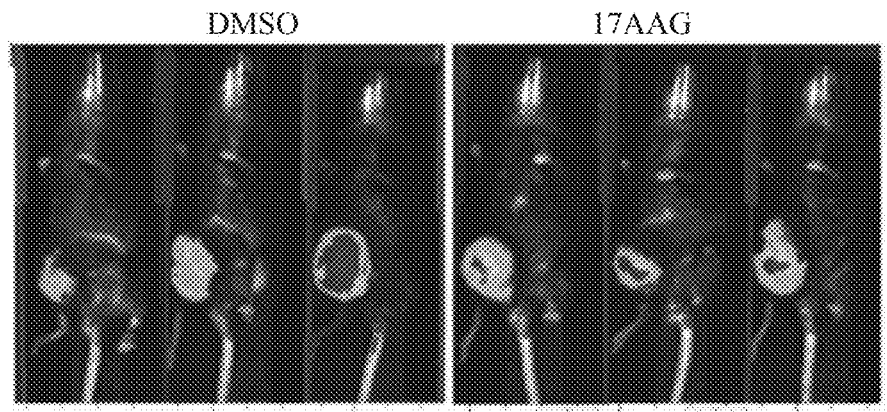
FIG. 6B-6E are images of three representative mice from each indicated group at the end of the treatment.
Figures 6D, 6E:
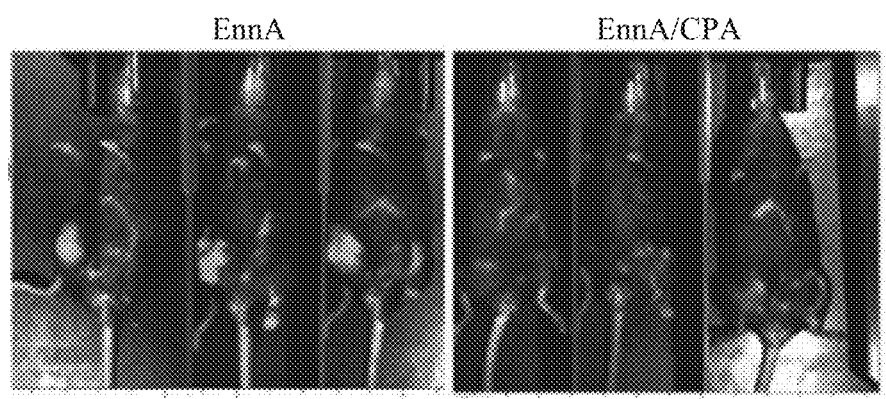
Figure 6F:
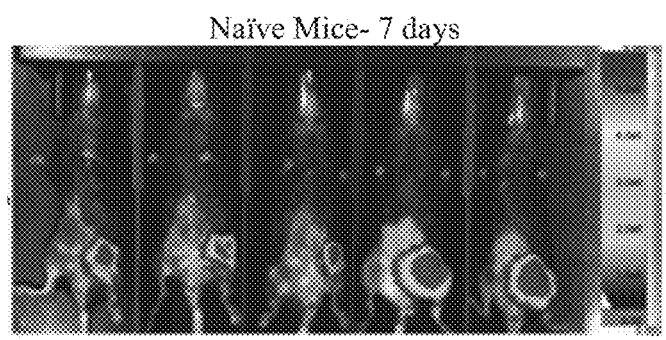
FIGS. 6F-6I are a panel of images of mice from the CPA+EnnA group monitored for tumor recurrence for two more months (3 months post implantation). No tumor recurrence was observed. They were re-challenged with 50,000 E0771 cells implanted in the opposite fat pad. Five Naïve mice were used as controls. Upper panels and lower show luciferase luminescence images of mice bearing tumors at 7 and 17 days after the second implantation, respectively.
Figure 6G:
Figure 6H:
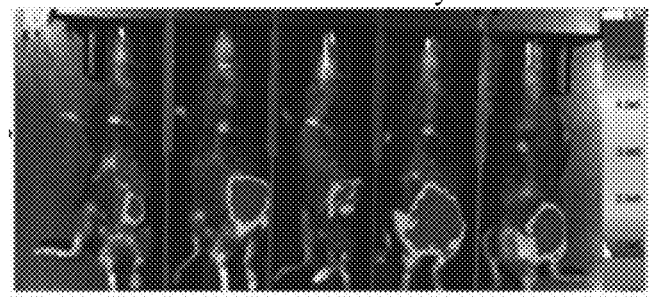
Figure 6I:
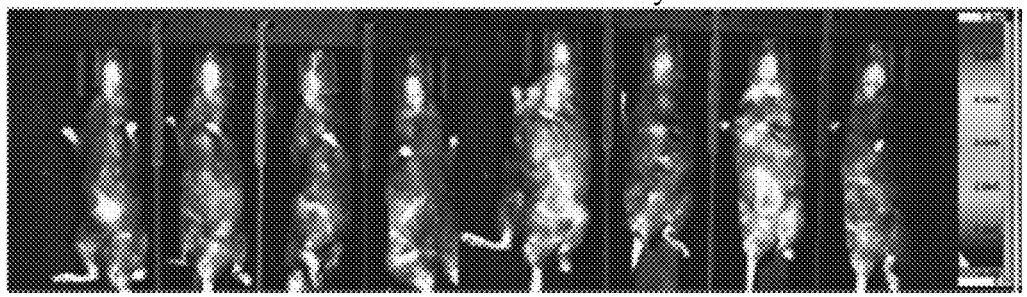
Figure 7E:
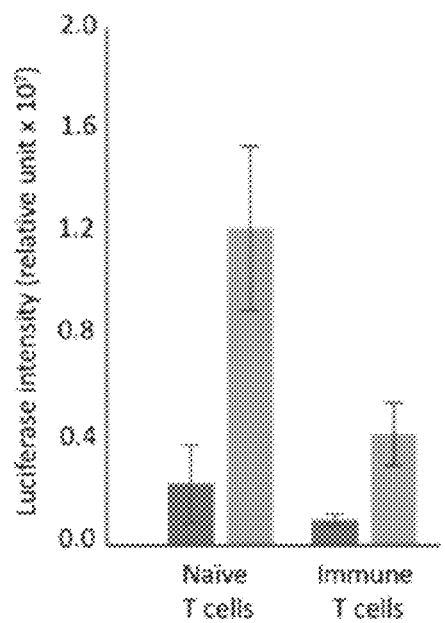
FIG. 7E is a graph showing the tumor volume as estimated by luciferase intensity.

The anti-tumor activity of EnnA involves both cytotoxicity and clearance by T cells. This is further supported by the fact that T cell depletion using an anti-CD8 antibody, restores an aggressive tumor growth in mice (FIG. 6A). Clearly, EnnA is more efficacious than 17-AAG (FIG. 6A-6D), and combination of EnnA with a single dose of cyclophosphamide (CPA) completely cured the mice (FIG. 6A, 6E). Indeed, EnnA/CPA-treated mice remained tumor-free for 2 months after the end of EnnA treatment. To test whether the cured mice developed immune memory, they were with 50,000 E0771 tumor cells. As shown in FIG. 6F-6G, seven days after the second implantation, tumors have grown in naïve control mice (n=5), but only two of the seven mice from EnnA/CPA-treated group showed small tumors, which were completely eliminated 10 days later (FIG. 6H-6I). Taken together, these results strongly suggest that EnnA kills breast tumors in mice through a cytotoxic effect that increases the immunogenicity of tumor cells, leading to (i) their destruction by T cells, and (ii) the creation of immune memory that prevents recurrence of the disease.

Figure 9A:
FIGS. 9A-9B are H&E stained lung sections from E0771 tumor bearing mice treated with DMSO (FIG. 9A) or EnnA (FIG. 9B).
Figure 9B:
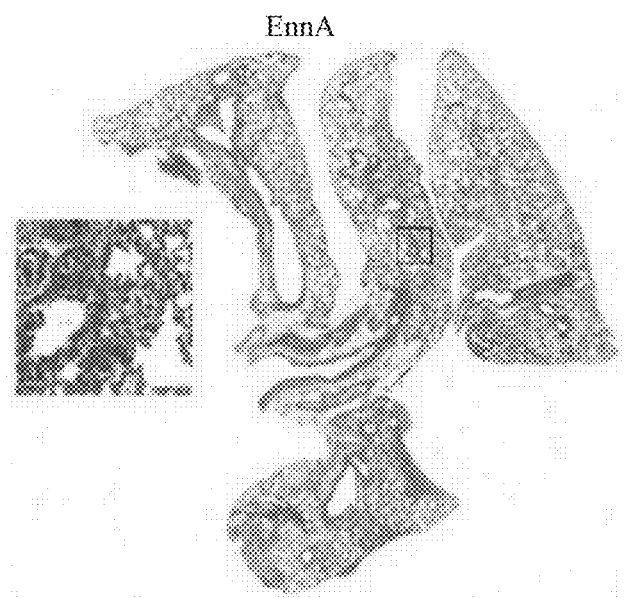
Figures 9C, 9D, 9E:
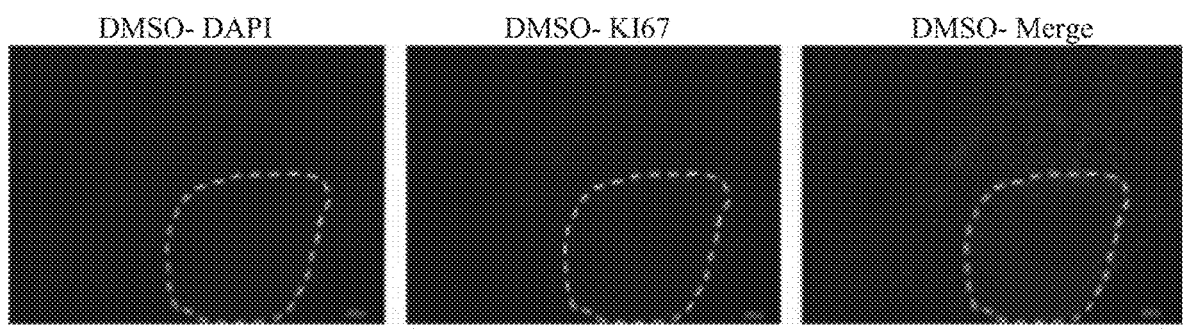
Figures 9F, 9G, 9H:
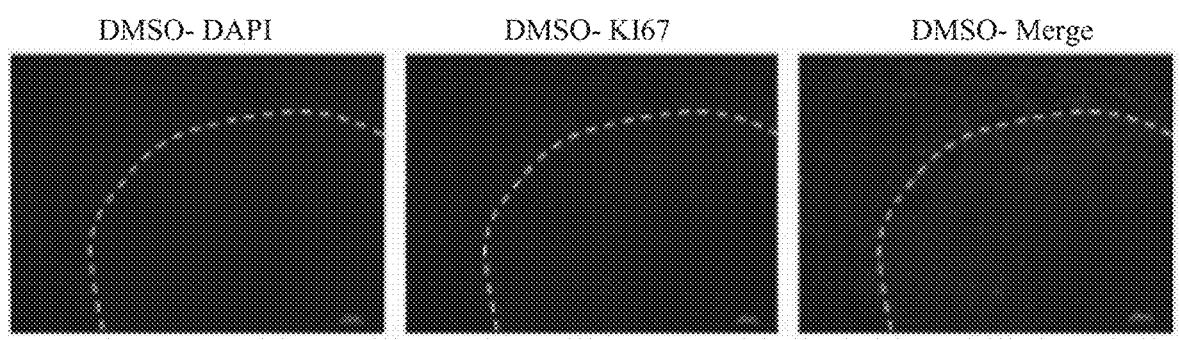
Figures 9U, 9V, 9W:
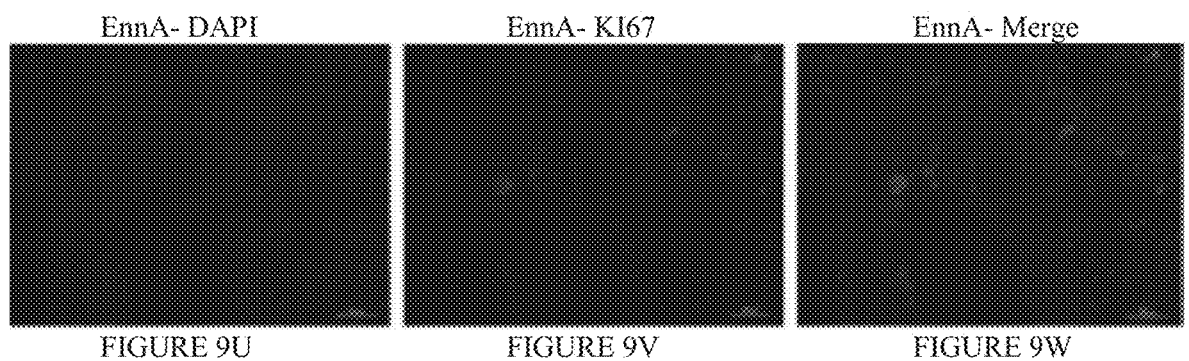
Figures 9X, 9Y, 9Z:
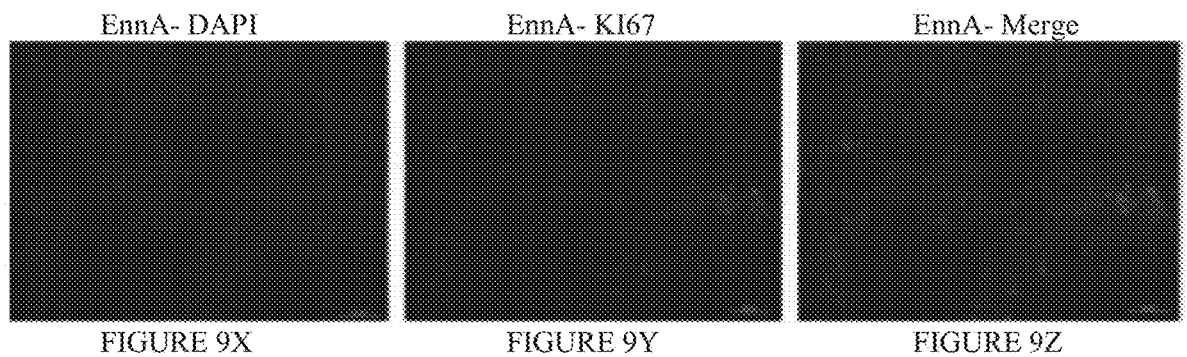

In addition, EnnA treatment prevents breast cancer metastasis to the lungs (FIG. 9A-9Z).

Example 6

EnnA Treatment Generates a Protective Transferable Immunity

Materials and Methods

Two groups of mice (n=10) were implanted with 50,000 E0771 cells expressing the luciferase reporter gene. Seven days post implanatation, animals were transferred with 10 million T cells isolated from the spleens of tumor-resistant mice in FIG. 6C, or from naïve tumor free animals. T cells were injected via tail vein. Tumors were imaged on day 7 (day 1 of T cells transfer) and on day 7 post T cells transfer.

Results

Results in FIG. 7A-7E show that T cells from animals treated with EnnA in combination with CPA are able to reduce the tumor growth compared to naïve T cells from animal controls. These results confirm the observation in FIGS. 5 and 6 that EnnA antitumor activity involves T cell immunity and suggests that EnnA treatment could promote T cell-based immunotherapy.

Example 7

EnnA Anti-Tumor Activity is Mediated by CD8β T Cells

Results

Figures 8A, 8B:
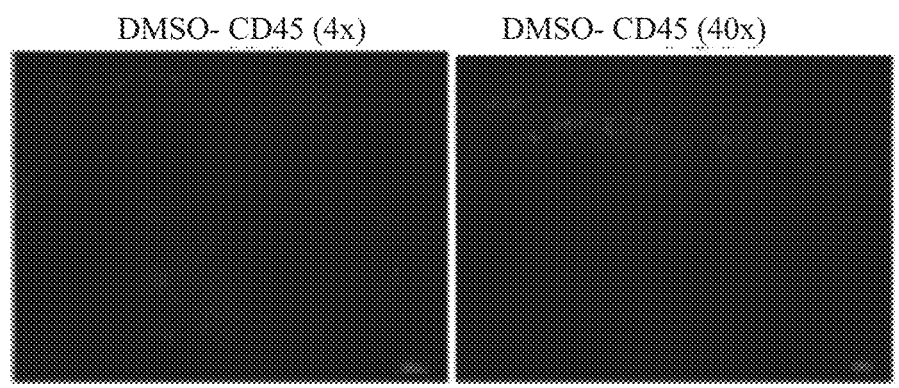
FIGS. 8A-8L show immunofluorescent staining of E0771 tumors using anti-CD45 and anti-CD8β antibodies.
Figures 8C, 8D:
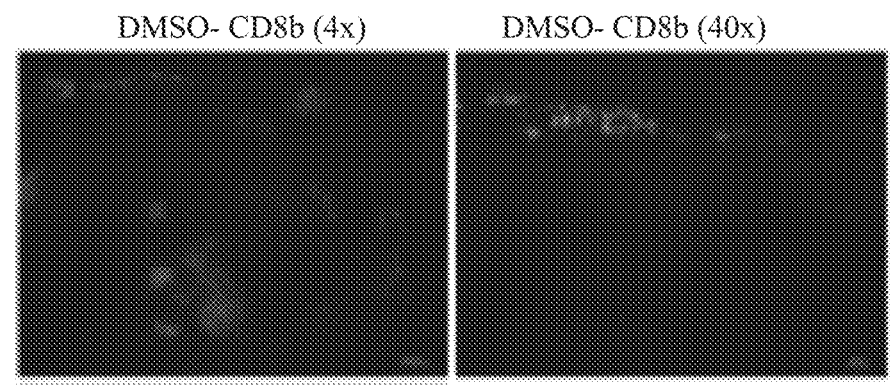
Figure 8E:
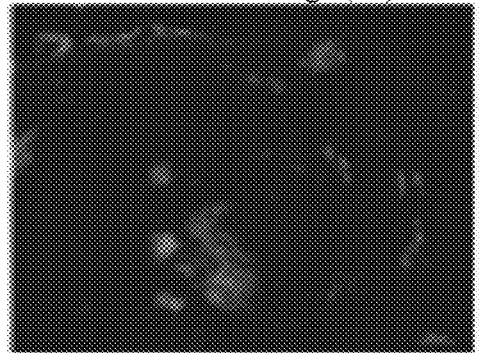
Figure 8F:
Figure 8G:
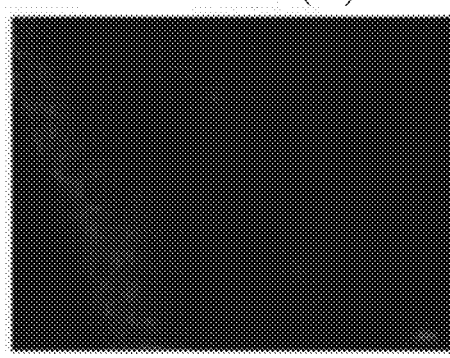
Figure 8H:
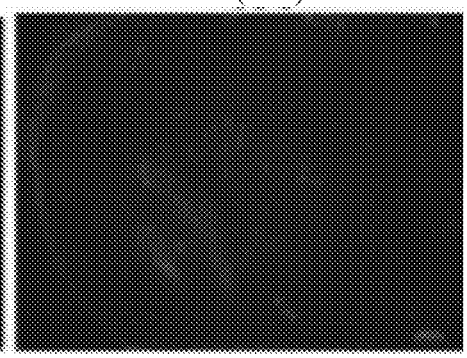
Figure 8I:
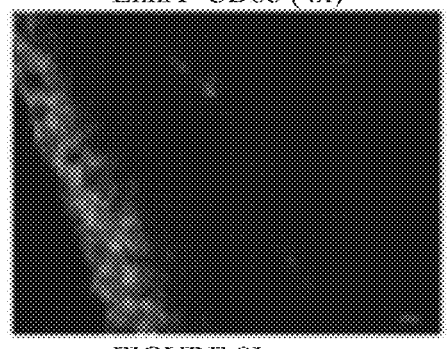
Figure 8J:
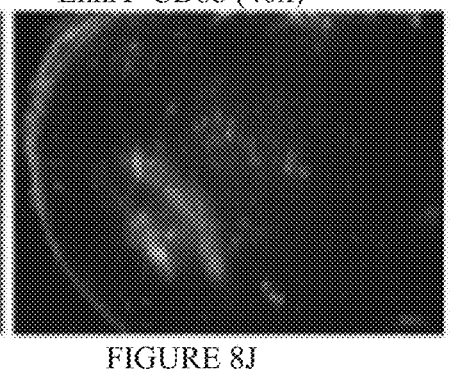
Figures 8K, 8L:
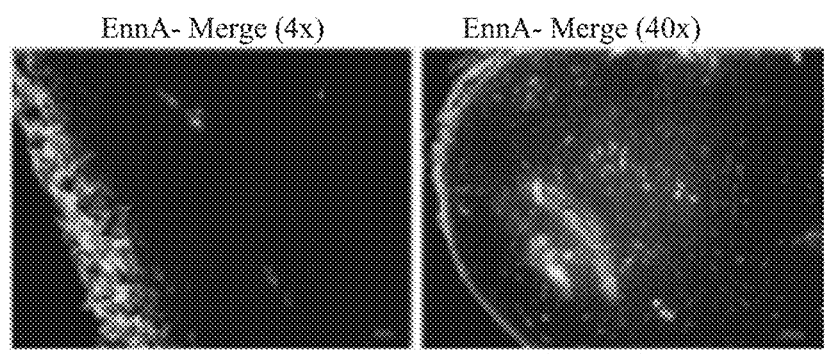
Figures 8M, 8N, 8O, 8P:
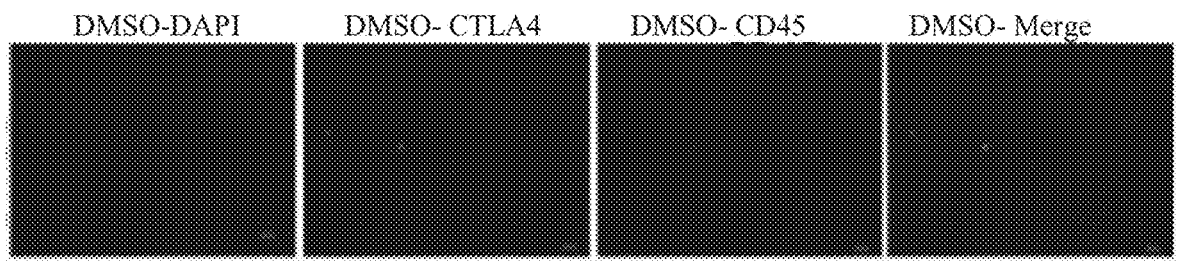
FIGS. 8M-8T show immunofluorescent staining of E0771 tumors using anti-CD45 and anti-CTLA-4 antibodies.
Figures 8Q, 8R, 8S, 8T:
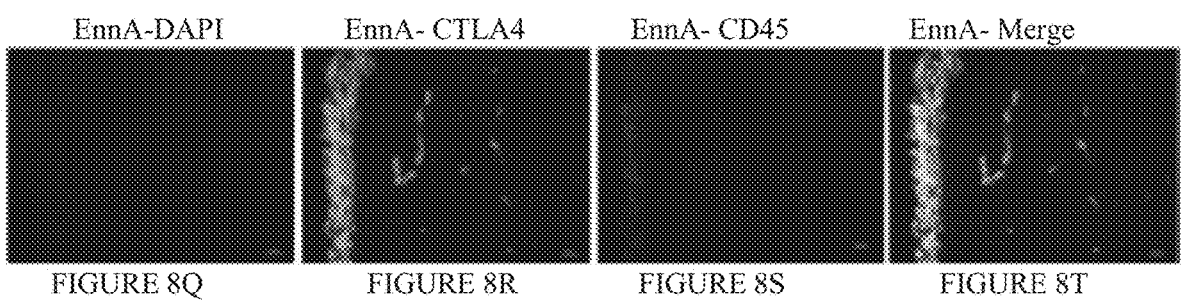
Figure 8U:
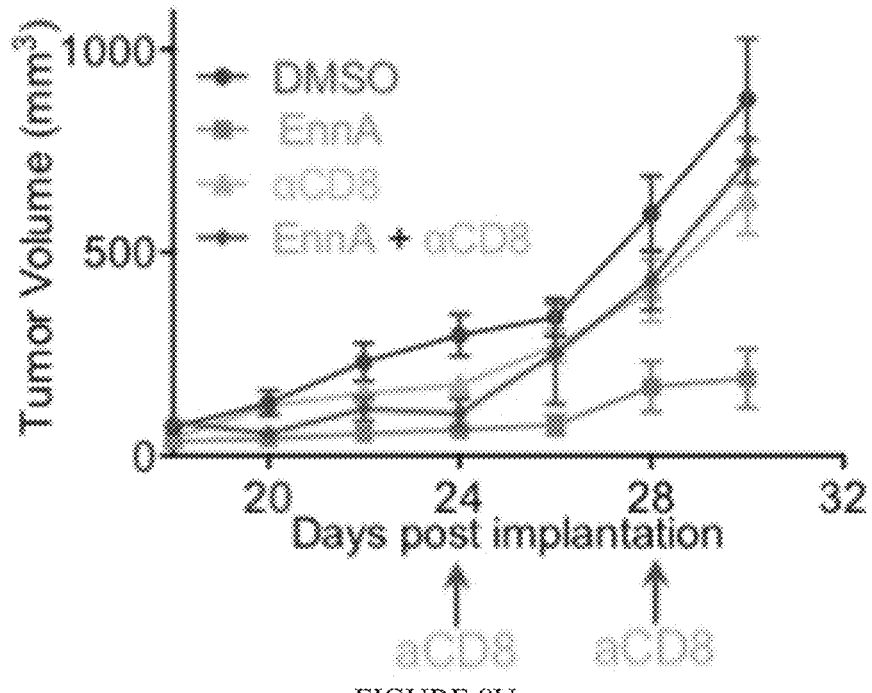
FIG. 8U is a line graph that shows tumor volume (mm$^3$) over time (days) for E0771 tumor-bearing mice treated with DMSO, EnnA, αCD8, or EnnA+αCD8.
Figure 8V:
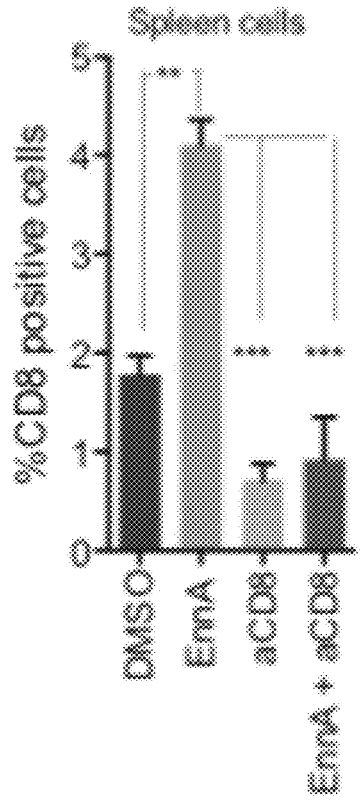
FIG. 8V is a bar graph showing the results of FACS analysis of CD8 positive cells in E0771 tumor-bearing mice treated with DMSO, EnnA, αCD8, or EnnA+αCD8. The X axis represents treatment group and the Y axis represents percent CD8 positive cells.

Further analysis of tumors showed that EnnA treatment induces higher infiltration of tumors with CD45+, CD8β+ T cells (FIG. 8A-8L) and T helper CD45+CD4+ T (not shown) cells. EnnA seems to reduce CD8β T cell exhaustion as indicated by reduced CD8β+PD-1+ and reduced suppression by lowering the proportion of CD4+, FoxP3+ Tregs in tumors. Compared to DMSO control, tumors from animal treated with EnnA are surrounded by a much higher number of CD45+, CD8β+ T cells that remain blocked in the periphery of tumors (FIG. 8M-8T). Together these data correlate with the finding that depletion of CD8 T cells by intraperitoneal injection of anti-CD8 monoclonal antibody leads to a rapid regrowth of tumors (FIG. 8U). In the periphery, analysis of splenocytes from tumor bearing animal showed that EnnA increase the proportion of CD8β (FIG. 8V) and CD4 T (not shown) cell in treated animals. T cell populations, CD8β+ in particular, play a key role in the mechanism of action EnnA probably through reduction of PD-L1/PD-1 signaling and reduced exhaustion. Overall, EnnA promotes T cells migration toward tumors, and to a certain extent better tumor infiltration (FIGS. 8A-8L).

Figure 8W:
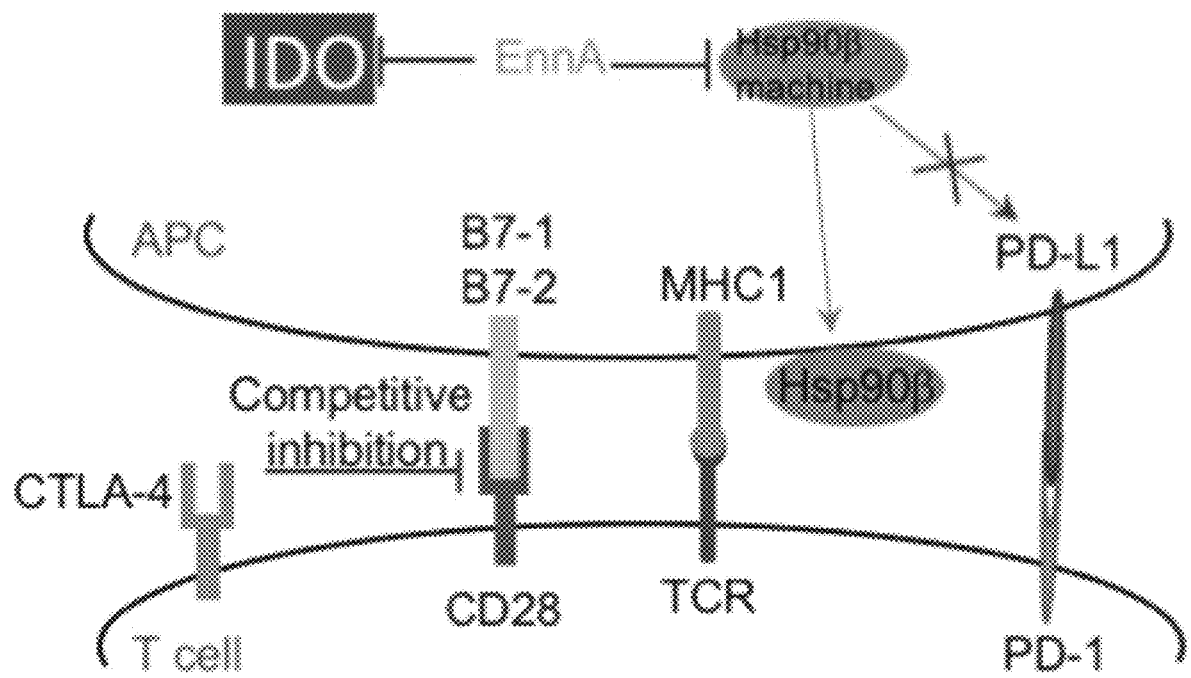
FIG. 8W is a model for EnnA inhibition of Hsp 90 machinery and its impacts on the immune suppressive mechanism through PD-1 and IDO.

Although moderate T cell tumore infiltration was observed with EnnA treatment, better therapeutic outcome could be achieved by improving T cell infiltration into tumors. One modality that has been shown to improve tumor infiltration is inhibition of cytotoxic T-lymphocyte-associated protein 4 (CTLA-4), which is upregulated as a response to TCR ligation and compete off CD28 for B7 binding leading to reduced stimulation by CD28 signaling (Krummel, M F and Allison, J P., *J Exp Med,* 182:459-465 (1995); Walunas, T L., et al., *Immunity,* 1:405-413 (1994)). CTLA-4 blockade expands infiltrating T cells and reduces regulatory T cells within melanoma tumors (Curran, M A., et al., *Proc Natl Acad Sci USA,* 107:4275-4280 (2010)). Combination of anti-PD1, which is induced later during T cell activation, and anti-CTLA-4 improves clinical therapeutic efficacy compared to either monotherapy (Postow, et al., *N Engl J Med,* 372:2006-2017 (2015); Larkin, J., et al., *N Engl J Med,* 373:23-34 (2015), Wolchok, J D., et al., *N Engl J Med,* 369:122-133)). This tremendous clinical progress has been attributed to the significant difference in the mechanism of action of these immunotherapies in melanoma and colon cancers (Wei; S C., et al., *Cell,* 170:1120-1133)). Anti-CTLA-4 induces expansion of ICOS+ Th1-like CD4 effector population and promotes their infiltration into tumors. Anti-PD-1 on the other hand seems to primarily acts through targeting CD8 T cell populations. Thus, the promotion of CTLA-positive population in the tumor microenvironment by EnnA was studied. As seen in FIGS. 8M-8T, immune cells within and surrounding the EnnA treated tumors co-express CD8β and CTLA-4. It was therefore hypothesized that combination of EnnA, which reduces the PD-1/PD-L1 signaling, and anti CTLA-4 blockade therapy might have a higher efficacy than either monotherapy (FIG. 8W). This combination might result in better efficacy than the combination of anti PD-1 and anti-CTLA-4, as EnnA has a broader effect than anti-PD-1 and exhibits an efficient cytoxicity in various breast cancer subtypes as well as in prostate cancer cell lines. EnnA can potentially broaden the spectrum of anti-CTLA-4 blockade to include various solid tumors including breast.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for reducing cancer cells in a subject having breast cancer, hepatoma, glioma, lymphoma or leukemia, comprising:
    administering to the subject an effective amount of a composition consisting of Enniatin A (EnnA) and
    a single dose of a potentiating agent, chemotherapeutic agent, or both to inhibit a Hsp90 machine without inducing an extensive cellular stress response.

2. The method of claim 1, wherein the effective amount of the composition inhibits or reduces proliferation of T regulatory cells and myeloid-derived suppressor cells (MDSCs) in tumor microenvironments.

3. The method of claim 1, wherein the effective amount of the composition reduces the mRNA and protein levels of Programmed death-ligand 1.

4. The method of claim 1, wherein the effective amount of the composition reduces proliferation of regulatory T cells and MDSCs in tumor microenvironments.

5. The method of claim 1, wherein the effective amount of the composition reduces the number of CD4+Foxp3+ T regulatory cells (Tregs) and CD11b+Gr-1+ MDSCs in tumors.

6. The method of claim 1, wherein the effective amount of the composition increases the immunogenicity of cancer cells.

7. The method of claim 1, wherein the effective amount increases the immunogenic cell death.

8. The method of claim 1, wherein the effective amount of the composition induces or promotes immune memory.

9. The method of claim 1, wherein the potentiating agent comprises cyclophosphamide.

10. The method of claim 1, wherein the effective amount of a composition consisting of Enniatin A (EnnA) is 5 µM to about 40 µM.

* * * * *